US008445649B2

(12) United States Patent
Hoshi et al.

(10) Patent No.: US 8,445,649 B2
(45) Date of Patent: May 21, 2013

(54) ANTIBODY AND USE THEREOF

(75) Inventors: Minako Hoshi, Kyoto (JP); Michio Sato, Tokyo (JP); Shoji Ideno, Osaka (JP); Koji Naito, Osaka (JP); Satoshi Horie, Osaka (JP); Munehiro Noda, Osaka (JP); Hajime Horii, Osaka (JP)

(73) Assignee: Tao Health Life Pharma Co., Ltd., Kyoto (JP)

( * ) Notice: Subject to any disclaimer, the term of this patent is extended or adjusted under 35 U.S.C. 154(b) by 187 days.

(21) Appl. No.: 12/734,359

(22) PCT Filed: Oct. 29, 2008

(86) PCT No.: PCT/JP2008/069696
§ 371 (c)(1),
(2), (4) Date: Jul. 21, 2010

(87) PCT Pub. No.: WO2009/057664
PCT Pub. Date: May 7, 2009

(65) Prior Publication Data
US 2010/0297662 A1 Nov. 25, 2010

(30) Foreign Application Priority Data
Oct. 29, 2007 (JP) .................................. 2007-280187

(51) Int. Cl.
C07K 16/18 (2006.01)
C12P 21/08 (2006.01)

(52) U.S. Cl.
USPC ...................... 530/388.1; 424/139.1; 530/809

(58) Field of Classification Search
None
See application file for complete search history.

(56) References Cited

U.S. PATENT DOCUMENTS

| | | | |
|---|---|---|---|
| 5,225,539 A | 7/1993 | Winter | |
| 6,548,640 B1 | 4/2003 | Winter | |
| 8,168,188 B1 * | 5/2012 | Hoshi et al. | 424/156.1 |
| 2003/0165496 A1 | 9/2003 | Basi et al. | |
| 2004/0127688 A1 | 7/2004 | Winter | |

FOREIGN PATENT DOCUMENTS

| | | |
|---|---|---|
| EP | 1 787 998 | 5/2007 |
| JP | 2912618 | 4/1999 |
| JP | 2001-247600 | 9/2001 |
| JP | 2002-105099 | 4/2002 |
| WO | 90/12871 | 11/1990 |
| WO | 02/46237 | 6/2002 |
| WO | 02/088306 | 11/2002 |
| WO | WO 2004/031400 | * 4/2004 |
| WO | 2006/016644 | 2/2006 |

OTHER PUBLICATIONS de la Torre JC., J Alzheimers Dis., 24(4):657-668, 2011.*

International Search Report issued Nov. 25, 2008 in International (PCT) Application No. PCT/JP2008/069696.
Jones, P.T. et al., *Replacing the complementarity-determining regions in a human antibody with those from a mouse*, Nature, vol. 321, No. 29 (May 1986), pp. 522-525.
Riechmann, L. et al., *Reshaping human antibodies for therapy*, Nature, vol. 332, No. 24 (Mar. 1988), pp. 323-327.
Verhoeyen, M. et al., *Reshaping Human Antibodies: Grafting an Antilysozyme Activity*, Science, vol. 239 (Mar. 25, 1988), pp. 1534-1536.
Sung Co., M. et al., *Humanized antibodies for antiviral therapy*, Proc. Natl. Acad. Sci. USA, vol. 88 (Apr. 1991), pp. 2869-2873.
Nakamura, Y. et al., *Codon usage tabulated from international DNA sequence databases: status for the year 2000*, Nucleic Acids Research, vol. 28, No. 1 (2000), p. 292.
Hoshi, Minako, *Katachi' ga Seigyo suru Shinkei no Shi*, Protein, Nucleic acid and Enzyme, vol. 49, No. 7 (May 2004), pp. 1098-1100.
Hoshi, M. et al., *Spherical aggregates of beta-amyloid (amylospheroid) show high neurotoxocity and activate tau protein kinase I/glycogen synthase kinase-3β*, Proc. Natl. Acad. Sci. USA, vol. 100, No. 11 (2003), pp. 6370-6375.
Hoshi, Minako, *β-amyloid Jiko Soshikika ni yoru Shinkei Dokusei no Hatsugen*, Kagaku to Kogyo, vol. 57, No. 5 (May 2004), pp. 519-521.
Kayed, R. et al., *Common Structure of Soluble Amyloid Oligomers Implied Common Mechanism of Pathogensis*, Science, vol. 300 (Apr. 18, 2003), pp. 486-490.
Lambert, M. P. et al., *Monoclonal antibodies that target pathological assemblies of Aβ*, Journal of Neurochemistry, vol. 100 (2007), pp. 23-35.
Barghorn, S. et al., *Globular amyloid β-peptide $_{1-42}$ oligomer—a homogenous and stable neuropathological protein in Alzheimer's disease*, Journal of Neurochemistry, vol. 95 (2005), pp. 834-847.
Lee, E. B. et al., *Targeting Amyloid-β Peptide (Aβ) Oligomers by Passive Immunization with a Conformation-selective Monoclonal Antibody Improves Leaning and Memory in Aβ Precursor Protein (APP) Transgenic Mice*, Journal of Biological Chemistry, vol. 281, No. 7 (Feb. 17, 2006), pp. 4292-4299.
Glabe, Charles G., *Structural Classification of Toxic Amyloid Oligomers*, Journal of Biological Chemistry, vol. 283, No. 44 (Oct. 31, 2008), pp. 29639-29643.
Hoshi, M., *Cognition and Dementia*, vol. 6, No. 4 (Oct. 2007), pp. 74-78 (with partial English translation).

(Continued)

Primary Examiner — Jeffrey Stucker
Assistant Examiner — Stacey N MacFarlane
(74) Attorney, Agent, or Firm — Wenderoth, Lind & Ponack, L.L.P.

(57) ABSTRACT

An antibody provided by the present invention has a low reactivity with amyloid precursor proteins, and has a higher reactivity with amylospheroids than with amyloid β fibrils or monomeric amyloid β-proteins. According to the present invention, an antibody is provided that has a higher reactivity with amylospheroids than with amyloid precursor proteins, and has any one or more of the following properties: (i) a higher activity with amylospheroids than with amyloid β fibrils; (ii) a higher reactivity with amylospheroids than with monomeric amyloid β-proteins; and (iii) an activity of inhibiting neuronal cell death induced by amylospheroids.

21 Claims, 15 Drawing Sheets

OTHER PUBLICATIONS

Japanese Office Action (with English translation) issued Sep. 11, 2012 in corresponding Japanese Patent Application No. 2009-539096.

Supplementary European Search Report mailed May 30, 2012 in corresponding European Application No. 08 84 4261.

Yuko Horikoshi, et al.; "Aβ N-Terminal-End Specific Antibody Reduced β-Amyloid in Alzheimer-Model Mice"; *Biochemical and Biophysical research Communications*; vol. 325, No. 2; p. 384-387; Academic Press, Inc.; c. Dec. 2004.

Yuko Horikoshi, et al.; "Development of Aβ Terminal End-Specific Antibodies and Sensitive ELISA for Aβ Variant"; *Biochemical and Biophysical research Communications*; vol. 319, No. 3; p. 733-737; Academic Press, Inc.; c. Jul. 2004.

Frédérique Bard et al.; "Peripherally Administered Antibodies Against Amyloid β-Peptide Enter the Central Nervous System and Reduce Pathology in a Mouse Model of Alzheimer Disease"; *Nature Medicine*; vol. 6, No. 8; p. 916-919; Nature Publishing Group; c. Aug. 2000.

D. Frenkel et al.; "High Affinity Binding of Monoclonal Antibodies to the Sequential Epitope EFRH of β-Amyloid Peptide is Essential for Modulation of Fibrillar Aggregation"; *Journal of Neuroimmunology*; vol. 95; p. 136-142; Elsevier Science Publishers; c. Jan. 1999.

Akihiko Noguchi et al.; "Isolation and Characterization of Patient-Derived, Toxic, High mass Amyloid β-Protein (Aβ) Assembly from Alzheimer Disease Brains"; *The Journal of Biological Chemistry*; vol. 284. No. 47; p. 32895-32905; The American Society for Biochemisty and Molecular Biology; c. Nov. 2009.

\* cited by examiner

The Epitope Analysis

| | ASD antibodies | | | N-terminal antibody (82E1) |
|---|---|---|---|---|
| | haASD1 | haASD2 | haASD3 | |
| Aβ1-5 | ND | ++++ | ND | ++++ |
| Aβ2-6 | ND | ND | ND | ND |
| Aβ3-7 | ND | ND | ND | ND |
| Aβ4-8 | ND | ND | ND | ND |
| Aβ5-9 | ND | ND | ND | ND |
| Aβ6-10 | ND | ND | ND | ND |
| Aβ7-11 | ND | ND | ND | ND |
| Aβ8-12 | ND | ND | ND | ND |
| Aβ9-13 | ND | ND | ND | ND |
| Aβ10-14 | ND | ND | ND | ND |
| Aβ11-15 | ND | ND | ND | ND |
| Aβ12-16 | ND | ND | ND | ND |
| Aβ13-17 | ND | ND | ND | ND |
| Aβ14-18 | ND | ND | ND | ND |
| Aβ15-19 | ND | ND | ND | ND |
| Aβ16-20 | ND | ND | ND | ND |
| Aβ17-21[a] | | | | |
| Aβ18-22[a] | | | | |
| Aβ19-23 | ND | ND | ND | ND |
| Aβ20-24 | ND | ND | ND | ND |
| Aβ21-25 | ND | ND | ND | ND |
| Aβ22-26 | ND | ND | ND | ND |
| Aβ23-27 | ND | ND | ND | ND |
| Aβ24-28 | ND | ND | ND | ND |
| Aβ25-29 | ND | ND | ND | ND |
| Aβ26-30 | ND | ND | ND | ND |
| Aβ27-31 | ND | ND | ND | ND |
| Aβ28-32 | ND | ND | ND | ND |
| Aβ29-33 | ND | ND | ND | ND |
| Aβ30-34 | ND | ND | ND | ND |
| Aβ31-35 | ND | ND | ND | ND |
| Aβ32-36 | ND | ND | ND | ND |
| Aβ33-37 | ND | ND | ND | ND |
| Aβ34-38 | ND | ND | ND | ND |
| Aβ35-39 | ND | ND | ND | ND |
| Aβ36-40 | ND | ND | ND | ND |
| Aβ37-41 | ND | ND | ND | ND |
| Aβ38-42 | ND | ND | ND | ND |

The symbols are; ++++, more than 75%; +++, 50-75%; ++, 25-50%; +, less than 25%; ND, not detected. a: not determined

FIG. 3

```
         10        20        30        40        50        60
GAAGTGCAGCTGGTCGAGTCTGGCGGCGGACTCGTGAAGCCTGGCGGCTCCCTGCGGCTG
 E  V  Q  L  V  E  S  G  G  G  L  V  K  P  G  G  S  L  R  L

=====CDR1======
         70        80        90       100       110       120
TCCTGCGCCGCCTCCGGCTTTACCTTCTCCGACTACTTCATGTCCTGGGTGCGGCAGGCT
 S  C  A  A  S  G  F  T  F  S  D  Y  F  M  S  W  V  R  Q  A

================================CDR2==
        130       140       150       160       170       180
CCTGGCAAGGGCCTGGAATGGGTCGGGGGGATCGAGATCAAGTCCTACTTCTACGCCACC
 P  G  K  G  L  E  W  V  G  G  I  E  I  K  S  Y  F  Y  A  T

===============================
        190       200       210       220       230       240
TACTACTTCGGCTCCGTGAAGGGCCGGTTCACCATCTCCCGGGACGACTCCAAGAACACC
 Y  Y  F  G  S  V  K  G  R  F  T  I  S  R  D  D  S  K  N  T 250       260       270       280       290       300
CTGTACCTGCAGATGAACTCCCTGAAAACCGAGGACACCGCCGTGTACTACTGCACCACC
 L  Y  L  Q  M  N  S  L  K  T  E  D  T  A  V  Y  Y  C  T  T

===========CDR3===========
        310       320       330       340       350       360
AACCGGGAAGTGGGGGGGCCTGGACAACTGGGGCCAGGGCACCCTGGTGACCGTGTCCTCC
 N  R  E  V  G  G  L  D  N  W  G  Q  G  T  L  V  T  V  S  S
```

FIG. 10

```
         10        20        30        40        50        60
CAGTCCGTGCTGACCCAGCCTTCCTCCCTGTCCGCCTCCCCTGGCGCCTCCGCCTCCCTG
 Q  S  V  L  T  Q  P  S  S  L  S  A  S  P  G  A  S  A  S  L

==============CDR1==========================
         70        80        90       100       110       120
ACCTGCACCCTGCGGTCCGGCATCTCCGTGGGCGGCAAGAACATCTACTGGTATCAGCAG
 T  C  T  L  R  S  G  I  S  V  G  G  K  N  I  Y  W  Y  Q  Q

==============CDR2========
        130       140       150       160       170       180
AAGCCTGGCTCCCCTCCTCAGTACCTGCTGAAGTACTCCTCCTACTCCAACAAGCAGCTG
 K  P  G  S  P  P  Q  Y  L  L  K  Y  S  S  Y  S  N  K  Q  L

======
        190       200       210       220       230       240
GGACCTGGCGTGCCTTCCCGGTTCTCCGGCTCCAAGGACGCCAGCGCCAACGCCGGCATC
 G  P  G  V  P  S  R  F  S  G  S  K  D  A  S  A  N  A  G  I

============
        250       260       270       280       290       300
CTGCTGATCTCTGGACTGCAGAGCGAGGACGAGGCCGACTACTACTGCTCCATCCACGAG
 L  L  I  S  G  L  Q  S  E  D  E  A  D  Y  Y  C  S  I  H  E

CDR3==========
        310       320       330       340       350       360
TCCAACGCCTACGTGTTTGGCGGCGGAACAAAGCTGACAGTCCTGGGCCGG
 S  N  A  Y  V  F  G  G  G  T  K  L  T  V  L  G  R
```

FIG. 11

```
                        CDR1=              ======CDR2=
     10        20        30        40        50        60
EVQLVESGGG LVKPGGSLRL SCAASGFTFS DYFMSWVRQA PGKGLEWVAG IEIKSYFYAT

======                              ==CDR3===
     70        80        90       100       110       120
YYFGSVKGRF TISRDDSKNT VYLQMNSLKT EDTAVYYCTR NREVGGLDNW GQGTLVTVSS
```

FIG. 12

```
                    ====CDR1=====              ===CDR2==
     10        20        30        40        50        60
QSVLTQPSSL SASPGASASL TCTLRSGISV GGKNIYWYQQ KPGSPPQFFL FYSSYSNKQL

==                              ==CDR3===
     70        80        90       100       110       120
GPGVPSRFSG SKDTSANAAI LLISGLQSED EADYYCSIHE SNAYVFGGGT KLTVLG
```

FIG. 13

```
            ====CDR1=====                    ===CDR2==
   10       20        30        40        50        60
QAVLTQPASL SASPGASASL TCTLRSGISV GGKNIYWYQQ KPGSPPQYLL RYSSYSNKQL

==                              ==CDR3===
   70       80        90       100       110       120
GPGVPSRFSG SKDASANAGI LLISGLQSED EADYYCSIHE SNAYVFGGGT KLTVLG
```

FIG. 14

Data are means ± SEM (n=3).
:p<0.01 vs. F12/PBS(-)-group (student's t-test)
*:p<0.05 vs. DF-ASPD/PBS(-)-group (student's t-test)

ANTIBODY AND USE THEREOF

This application is a U.S. national stage of International Application No. PCT/JP2008/069696 filed Oct. 29,2008.

TECHNICAL FIELD

The present invention relates to a novel antibody having a low reactivity with amyloid precursor proteins and having a high reactivity with amylospheroids, and relates to the use of the same.

BACKGROUND ART

At present, "abnormal structural proteins" have drawn attention as common mechanisms of developing a plurality of neurodegenerative diseases that develop with aging, such as Alzheimer's disease, Parkinson's disease, Huntington's chorea, and prion disease, and molecular nature of such proteins has been studied. Deposition of the following two types of fibrillar aggregates in the brain has been reported as the pathological feature of Alzheimer's disease: senile plaque primarily composed of amyloid β-proteins (Aβ) (see Selkoe, D. J., Annu Rev. Neurosci., 12, 463-490, (1989); and Glenner, G. G. and Wong, C. W, Biochem. Biophys. Res. Commun., 120 (3), 885-890, (1984)); and neurofibrillary tangles (paired helical filament (PHF)) primarily composed of phosphorylated tau-proteins (see Ihara, Y. et al., J. Biochem., 99, 1807-1810, (1986); and Grundke-Iqbal, I. et al., Proc. Natl. Acad. Sci. U.S.A., 83, 4913-4917, (1986)). As to Alzheimer's disease, which has been considered being caused by a plurality of various pathogeneses, it is now considered through recent studies that the aggregation of amyloid β-proteins should be a common pathway for the development of all such pathogeneses. Amyloid β-protein is a peptide that is cleaved as a molecular species consisting of 40 (Aβ1-40) or 42 (Aβ1-42) residues from its precursor substance (i.e., amyloid precursor proteins (APP)), and the processes of generation and decomposition of amyloid β-proteins as monomers advance homeostatically even in normal humans. In Alzheimer's disease, however, amyloid β-proteins aggregate, and excessive deposition of amyloid β-proteins is observed in the end. This is considered to result from dysregulation during cleavage or decomposition. In the present specification, the former proteins ($A\beta_{1-40}$) are referred to as "amyloid β40", "amyloid β40 monomers", or "monomeric amyloid β40-proteins" in some cases, and the latter proteins ($A\beta_{1-42}$) are referred to as "amyloid β42", "amyloid β42 monomers", or "monomeric amyloid β42-proteins" in some cases. The amyloid β-proteins are cleaved as a molecular species consisting of 43 ($A\beta_{1-43}$) residues, though in minute quantities, and such proteins may be referred to as "amyloid β43", "amyloid β43 monomers", or "monomeric amyloid β43-proteins" in some cases.

The amyloid β-proteins having aggregated act on neurons as neurotoxins and cause synaptic degeneration and subsequent neuronal cell death. This mechanism is considered to cause neuronal loss, which may cause progressive cognitive disorder of Alzheimer's disease. Also, it has been reported that amyloid β-proteins do not exhibit neuronal cell death activity when they were released extracellularly as water-soluble monomeric peptides (hereinafter in the present specification the term "neuronal cell death activity" may be referred to as "toxicity") and that amyloid β-proteins self-assemble and form amyloid β fibrils, upon which they acquire toxicity (see Lorenzo, A. and Yankner, B. A., Proc. Natl. Acad. Sci. U.S.A., 91, 12243-12247, (1994)). Since it is known that cultured neurons are led to death when a solution containing toxic amyloid β-proteins that contains amyloid β fibrils is added at a high concentration thereto, the amyloid β fibrils have been considered to be the entity to induce neuronal cell death in Alzheimer's disease.

Thus, an experimental system that adds toxic amyloid β-proteins containing amyloid fibrils to neuronal cells and the like so as to induce death of these cells has been considered to reflect the neuronal cell death in Alzheimer's disease and has often been employed in screening inhibitors of neuronal cell death or the like. In recent years, however, the following facts have been reported, which would suggest that the toxic entity of the amyloid β-proteins is not the amyloid β fibrils. That is, (1) the concentration of amyloid β fibrils in a toxic amyloid β-protein-containing solution necessary for inducing neuronal cell death is several tens of μM (see Yankner, B. A., et al., Science, 250, 279-282, (1990)), which is 1,000 times or greater than the concentration of amyloid β-proteins in the brains of patients with Alzheimer's disease; (2) the amount of amyloid β fibrils deposited in the brains of patients with Alzheimer's disease is not always correlated with the impairment of higher-order functions, such as memory or cognitive function, and no clinical symptom may be developed in some cases even though a large amount of amyloid β fibrils are deposited; (3) the site of amyloid β deposition is not always consistent with the site of neuronal drop out in the brain; (4) abnormality is observed in learned behavior before or without the deposition of amyloid β fibrils in the brains of APP-overexpressing mice; and (5) increase in the water-soluble amyloid β-protein content in the brains of patients of Alzheimer's disease occurs 10 or more years ahead of the deposition of water-insoluble fibrils.

The present inventors had proposed a solution containing highly toxic self-assembling amyloid β-proteins that would induce neuronal cell death at a concentration equivalent to that of the amyloid β-proteins that have self-assembled and that exist in the bodies of patients of Alzheimer's disease or other diseases, and had proposed a method for producing such a solution (JP 2001-247600 A). The present inventors had also discovered a method for isolating a neurotoxic entity contained in the aforementioned solution containing self-assembling amyloid β-proteins, and analyzed the same. As a result, such neurotoxins were found to be self-assembling amyloid β-proteins in the form of particles having diameters of approximately 10 nm to 20 nm, and these particles were designated as amylospheroid (see Hoshi, M., et al., Proc. Natl. Acad. Sci. U.S.A., 100, 6370-6375 (2003)). In accordance with such designation, a self-assembling amyloid β-protein in the form of particles having diameters of approximately 10 nm to 20 nm is referred to as "amylospheroid" in some cases in the present specification.

Amylospheroids induce neuronal cell death at a concentration equivalent to that of amyloid β-proteins that exist in the brains of patients of Alzheimer's disease, and cause phosphorylation of tau-proteins, which is another pathological marker in the process where nerves are caused to die. Since these mechanisms are consistent with the pathological conditions of Alzheimer's disease, amylospheroids were considered to be the entity of toxicity of the amyloid β-proteins in the brains. If (1) an antibody that inhibits amylospheroid formation or (2) an antibody that inhibits toxicity of amylospheroids against neuronal cells is obtained, accordingly, such an antibody can be used as a therapeutic or preventive agent for Alzheimer's disease. If (3) an antibody having a higher reactivity with amylospheroids than with amyloid precursor proteins, amyloid β monomers, or amyloid β fibrils is obtained, such an antibody can be utilized in the assay for diagnosing Alzheimer's disease.

A method for preparing an antibody that reacts with amylospheroids as an antigen is a known method indeed. Besides, rabbit polyclonal anti-amylospheroid antibodies (ASD2, ASD3), and mouse monoclonal anti-amylospheroid antibodies (MASD1, MASD2, MASD3) have been obtained already (WO 2006/016644) (hereinafter an antibody that reacts with amylospheroids is referred to as "anti-amylospheroid antibody" in some cases). However, an antibody has not yet obtained that has a low reactivity with amyloid precursor proteins, that has a specific reactivity with amylospheroids, and that inhibits the toxicity of the foregoing proteins against neuronal cells. It should be noted that the rabbit polyclonal anti-amylospheroid antibodies (ASD2, ASD3) and mouse monoclonal anti-amylospheroid antibodies (MASD1, MASD2, MASD3) disclosed in WO 2006/016644 are hereinafter referred to as the following in the present specification:

ASD2→rpASD2
ASD3→rpASD3
MASD1→mASD1
MASD2→mASD2
MASD3→mASD3

Non-Patent Document 1: Selkoe, D. J., Annu. Rev. Neurosci., 12, 463-490 (1989)
Non-Patent Document 2: Glenner, G. G. and Wong, C. W, Biochem. Biophys. Res. Commun., 120 (3), 885-890 (1984)
Non-Patent Document 3: Ihara, Y. et al., J. Biochem., 99, 1807-1810 (1986)
Non-Patent Document 4: Grundke-Iqbal, I. et al., Proc. Natl. Acad. Sci. USA., 83, 4913-4917 (1986)
Non-Patent Document 5: Lorenzo, A and Yankner, B. A, Proc. Natl. Acad. Sci. USA, 91, 12243-12247 (1994)
Non-Patent Document 6: Yankner, B. A., et. al., Science, 250, 279-282 (1990)
Non-Patent Document 7: Hoshi, M., et. al., Proc. Natl. Acad. Sci. U.S.A., 100, 6370-6375 (2003)
Patent Document 1: JP 2001-247600 A
Patent Document 2: WO2006/016644

DISCLOSURE OF INVENTION

Problem to be Solved by the Invention

An object of the present invention is to obtain an antibody having a higher reactivity with amylospheroids than with amyloid precursor proteins, and having a higher reactivity with amylospheroids than with amyloid β fibrils or monomeric amyloid β-proteins; or an antibody having a higher reactivity with amylospheroids than with amyloid precursor proteins, and having an activity of inhibiting the neuronal cell death induced by amylospheroids. Another object of the present invention is to provide a method for screening a therapeutic/preventive agent for Alzheimer's disease with use of the aforementioned antibody, and a method for detecting an individual suffering from Alzheimer's disease with use of the aforementioned antibody. Still another object of the present invention is to provide a medicine in which the aforementioned antibody is used, such as a neuron protector, a reagent for detecting Alzheimer's disease, and a therapeutic and/or preventive agent for Alzheimer's disease. Still another object of the present invention is to provide a solid-phase support for detecting the aforementioned antibody. Still another object of the present invention is to provide a hybridoma for producing the aforementioned antibody.

Means for Solving Problem

The present inventors have conducted concentrated studies in order to achieve the above objects. Specifically, they immunized hamsters subcutaneously with amylospheroids, obtained splenic cells from the hamsters, and obtained a monoclonal antibody produced from a hybridoma established from the splenic cells. Consequently, they discovered that this antibody had a low reactivity with amyloid precursor proteins and a higher reactivity with amylospheroids than with amyloid β fibrils or monomeric amyloid β-proteins, and had an activity of inhibiting the neuronal cell death induced by amylospheroids. They also discovered that this antibody had a low cross-reactivity with human normal tissues, and reacted specifically with Alzheimer's disease brains. The present invention has been completed based on such findings.

Specifically, the present invention provides the following inventions.

(1) An antibody having a higher reactivity with amylospheroid than with amyloid precursor proteins, and having any one or more of the following properties:

(i) a higher activity with amylospheroid than with amyloid β fibrils;

(ii) a higher reactivity with amylospheroid than with monomeric amyloid β-proteins; and (iii) an activity of inhibiting the neuronal cell death induced by amylospheroid.

(2) The antibody according to (1), exhibiting a reactivity with amylospheroid at least 3 times higher than its reactivity with amyloid β fibrils, in a system wherein a reactivity of an antibody with amylospheroid is compared with a reactivity of the antibody with amyloid β fibrils at the same antibody concentration, antibody amount, antigen protein concentration, and antigen protein amount.

(3) The antibody according to (1) or (2), exhibiting a reactivity with amylospheroid at least 5 times higher than its reactivity with amyloid β fibrils, in a system wherein a reactivity of an antibody with amylospheroid is compared with a reactivity of the antibody with amyloid β fibrils at the same antibody concentration, antibody amount, antigen protein concentration, and antigen protein amount.

(4) The antibody according to any one of (1) to (3), exhibiting a reactivity with amylospheroid at least 50 times higher than its reactivity with monomeric amyloid β-proteins, in a system wherein a reactivity of an antibody with amylospheroid is compared with a reactivity of the antibody with monomeric amyloid β-proteins at the same antibody concentration, antibody amount, antigen protein concentration, and antigen protein amount.

(5) The antibody according to any one of (1) to (4), exhibiting a reactivity with amylospheroid at least 500 times higher than its reactivity with monomeric amyloid β-proteins, in a system wherein a reactivity of an antibody with amylospheroid is compared with a reactivity of the antibody with monomeric amyloid β-proteins at the same antibody concentration, antibody amount, antigen protein concentration, and antigen protein amount.

(6) The antibody according to any one of (1) to (5), being obtained using amylospheroid as an antigen.

(7) The antibody according to any one of (1) to (6), being a monoclonal antibody.

(8) The antibody according to (7), having a dissociation constant with amylospheroid of not more than $10^{-9}$.

(9) The antibody according to any one of (1) to (8), reacting specifically with Alzheimer's disease brains while not exhibiting a significant cross-reactivity with human normal tissues.

(10) The antibody according to any one of (1) to (9), recognizing an epitope specific to a tertiary structure of amylospheroid.

(11) The antibody according to any one of (1) to (10), obtained from a hamster.

(12) The antibody according to any one of (1) to (11), being a monoclonal antibody produced from a hybridoma having an accession number of either FERM BP-10871 or FERM BP-10872.

(13) A humanized antibody obtained by humanization of a hamster monoclonal antibody produced from a hybridoma having an accession number of either FERM BP-10871 or FERM BP-10872.

(14) The humanized antibody according to (13), or a fragment of the humanized antibody according to (13), comprising a humanized heavy chain and a humanized light chain, the humanized heavy chain including:

three heavy chain complementarity-determining regions (CDRs) obtained from a hamster monoclonal antibody produced from the hybridoma having the accession number of FERM BP-10872, the three heavy chain CDRs being heavy chain CDRs 1 to 3; and a heavy chain variable domain framework sequence obtained from a human immunoglobulin heavy chain; and the humanized light chain including;

three light chain complementarity-determining regions (CDRs) obtained from a hamster monoclonal antibody produced from the hybridoma having the accession number of FERM BP-10872, the three light chain CDRs being light chain CDRs 1 to 3; and a light chain variable domain framework sequence obtained from a human immunoglobulin light chain, wherein the three heavy chain CDRs 1 to 3 have the following amino acid sequences, respectively:

```
                                             (SEQ ID NO: 11)
heavy chain CDR1: Asp Tyr Phe Met Ser;

(SEQ ID NO: 12)
heavy chain CDR2: Gly Ile Glu Ile Lys Ser Tyr Phe
Tyr Ala Thr Tyr Tyr Phe Gly Ser Val Lys Gly;
and (SEQ ID NO: 13)
heavy chain CDR3: Asn Arg Glu Val Gly Gly Leu Asp
Asn,
``` and the three light chain CDRs 1 to 3 have the following amino acid sequences, respectively:

```
                                             (SEQ ID NO: 14)
light chain CDR1: Thr Leu Arg Ser Gly Ile Ser Val
Gly Gly Lys Asn Ile Tyr;

(SEQ ID NO: 15)
light chain CDR2: Tyr Ser Ser Tyr Ser Asn Lys Gln
Leu Gly Pro;
and (SEQ ID NO: 16)
light chain CDR3: Ser Ile His Glu Ser Asn Ala Tyr
Val.
```

(15) The humanized antibody according to (13), or a fragment of the humanized antibody according to (13), comprising a humanized heavy chain variable domain having an amino acid sequence according to SEQ ID NO: 17; and a light chain variable domain having an amino acid sequence according to SEQ ID NO: 18, wherein the amino acid sequence according to SEQ ID NO: 17 is as follows:

```
[Chemical Formula 1]
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Phe Met Ser Trp Val Arg Gln Ala Pro Gly Lys Gly Leu Glu Trp Val
        35                  40                  45

Xaa Gly Ile Glu Ile Lys Ser Tyr Phe Tyr Ala Thr Tyr Tyr Phe Gly
    50                  55                  60

Ser Val Lys Gly Arg Phe Thr Ile Ser Arg Asp Asp Ser Lys Asn Thr
65                  70                  75                  80

Xaa Tyr Leu Gln Met Asn Ser Leu Lys Thr Glu Asp Thr Ala Val Tyr
                85                  90                  95

Tyr Cys Thr Xaa Asn Arg Glu Val Gly Gly Leu Asp Asn Trp Gly Gln
            100                 105                 110

Gly Thr Leu Val Thr Val Ser Ser
        115                 120
``` where "Xaa" at position 49 is Gly or Ala, "X" at position 81 is Leu or Val, and "Xaa" at position 100 is Thr or Arg, and the amino acid sequence according to SEQ ID NO. 18 is as follows:

```
[Chemical Formula 2]
Gln Xaa Val Leu Thr Gln Pro Xaa Ser Leu Ser Ala Ser Pro Gly Ala
1               5                   10                  15
```

-continued

```
Ser Ala Ser Leu Thr Cys Thr Leu Arg Ser Gly Ile Ser Val Gly Gly
 20              25                  30

Lys Asn Ile Tyr Trp Tyr Gln Gln Lys Pro Gly Ser Pro Pro Gln Xaa
         35                  40                  45

Xaa Leu Xaa Tyr Ser Ser Tyr Ser Asn Lys Gln Leu Gly Pro Gly Val
     50                  55                  60

Pro Ser Arg Phe Ser Gly Ser Lys Asp Xaa Ser Ala Asn Ala Xaa Ile
 65                  70                  75                  80

Leu Leu Ile Ser Gly Leu Gln Ser Glu Asp Glu Ala Asp Tyr Tyr Cys
             85                  90                  95

Ser Ile His Glu Ser Asn Ala Tyr Val Phe Gly Gly Gly Thr Lys Leu
            100                 105                 110

Thr Val Leu Gly
        115
``` where "Xaa" at position 2 is Ser or Ala, "Xaa" at position 8 is Ser or Ala, "Xaa" at position 48 is Tyr or Phe, "Xaa" at position 49 is Leu or Phe, "Xaa" at position 51 is Lys, Phe, or Arg, "Xaa" at position 74 is Ala or Thr, and "Xaa" at position 79 is Gly or Ala.

(16) The humanized antibody or the fragment according to (15),
wherein the humanized heavy chain variable domain has an amino acid sequence according to SEQ ID NO: 5, and
the light chain variable domain has an amino acid sequence according to SEQ ID NO: 7.

(17) A method for screening a therapeutic and/or preventive agent for Alzheimer's disease, the method comprising:
bringing examined substances and the antibody according to any one of (1) to (16) into contact with amylospheroid; and
selecting a candidate substance from the examined substances, by referring to binding properties of the examined substances with amylospheroid, as indicators.

(18) A method for detecting an individual with Alzheimer's disease, the method comprising:
bringing a biological sample obtained from an individual suspected of Alzheimer's disease into contact with the antibody according to any one of (1) to (16); and
determining whether or not a substance that reacts with the antibody exists in the sample.

(19) A neuron protector comprising the antibody according to any one of (1) to (16).

(20) A reagent for detecting Alzheimer's disease, comprising the antibody according to any one of (1) to (16).

(21) A medicine comprising the antibody according to any one of (1) to (16).

(22) A therapeutic and/or preventive agent for Alzheimer's disease, comprising the antibody according to any one of (1) to (16).

(23) A solid-phase support used for detecting the antibody according to any of (1) to (16), the solid-phase support being coated with amylospheroid.

(24) A hybridoma for producing the antibody according to (7) or (8).

(25) A hybridoma having an accession number of either FERM BP-10871 or FERM BP-10872.

(26) A nucleic acid comprising a sequence that encodes a heavy chain or a light chain of the humanized antibody according to any one of (13) to (16), or a fragment of the sequence.

(27) An expression vector for expressing the humanized antibody or the fragment thereof according to any one of (13) to (16), comprising a nucleotide sequence that encodes the antibody or the fragment thereof.

EFFECTS OF THE INVENTION

The antibody of the present invention has a low reactivity with amyloid precursor proteins, a higher reactivity with amylospheroids than with amyloid β fibrils or with monomeric amyloid β-proteins, and has an activity of inhibiting the neuronal cell death induced by amylospheroids. Therefore, this antibody can be used as a therapeutic or preventive agent for Alzheimer's disease, and can be applied to the detection of an individual suffering from Alzheimer's disease.

DESCRIPTION OF THE INVENTION

The antibody of the present invention is an antibody that has a higher reactivity with amylospheroids than with amyloid precursor proteins, and has any one or more of the following properties (hereinafter such an antibody is referred to as "anti-amylospheroid specific antibody" in some cases):
(i) a higher activity with amylospheroids than with amyloid β fibrils;
(ii) a higher reactivity with amylospheroids than with monomeric amyloid β-proteins; and
(iii) an activity of inhibiting the neuronal cell death induced by amylospheroids.

The present invention further relates to a method for screening a therapeutic and/or preventive agent for Alzheimer's disease, a method for detecting an individual suffering from Alzheimer's disease, and a medicine such as a therapeutic and/or preventive agent for Alzheimer's disease, in each of which the aforementioned antibody is used, as well as relates to a hybridoma for producing the aforementioned antibody. These are described below in detail; however, the following merely describes exemplary embodiments (representative examples) of the present invention, and the scope of the present invention is not limited to the contents described in the following.

(1) Anti-Amylospheroid Specific Antibody

The anti-amylospheroid specific antibody of the present invention has a higher reactivity with amylospheroids than with amyloid precursor proteins, and further has the following aspects.

According to the first aspect of the present invention, the anti-amylospheroid specific antibody of the present invention has a higher reactivity with amylospheroids than with amyloid β fibrils. The term "reactivity with amylospheroids"

means that the antibody reacts with amylospheroids formed by the method described below. The reactivity of said antibody can be assayed by a common technique. If a reactivity of the antibody with amylospheroids is greater than that with amyloid β fibrils when the reactivity is assayed by such a technique, the antibody of interest is within the scope of the present invention. According to a preferred aspect, a reactivity of the antibody with amylospheroids is at least 3 times, more preferably at least 4 times, and most preferably 5 times higher than its reactivity with amyloid β fibrils. In such a case, the comparison can be performed as to the reactivities determined under the conditions of the same antibody concentration, antibody amount, antigen protein concentration, and antigen protein amount. An antibody that reacts specifically with amylospheroids but does not react with amyloid β fibrils also is included in the scope of the anti-amylospheroid specific antibody of the present invention.

According to a second aspect of the present invention, the anti-amylospheroid specific antibody of the present invention has a higher reactivity with amylospheroids than with monomeric amyloid β-proteins. In such a case, a reactivity of the anti-amylospheroid specific antibody with amylospheroids is preferably at least 50 times, more preferably at least 100 times, and most preferably at least 500 times higher than its reactivity with monomeric amyloid β-proteins (Aβ). In such a case, the comparison can be performed as to the reactivities determined under the conditions of the same antibody concentration, antibody amount, antigen protein concentration, and antigen protein amount.

Regarding the administration of an anti-Aβ antibody to Alzheimer's disease model animals or in clinical examinations, it has been confirmed that cerebral hemorrhage is induced by such administration. This hemorrhage is considered resulting from an inflammatory response to the binding of the antibody with cerebrovascular amyloid, and hence it is a side effect of the therapy with use of the anti-Aβ antibody. The deposition of cerebrovascular amyloid is observed in 80 to 90% of the patients with Alzheimer's disease, and is called "Aβ-type Cerebral Amyloid Angiopathy (CAA)". Amyloids in senile plaque in Alzheimer's disease are primarily composed of Aβ42, whereas amyloids in the deposition in CAA are primarily composed of Aβ40. In view of this, preferably the antibody of the present invention selectively reacts with amylospheroids in particular, and has a low reactivity with Aβ40. Specifically, the reactivity of the anti-amylospheroid specific antibody of the present invention with amylospheroids preferably is at least 50 times higher than its reactivity with Aβ40, more preferably at least 100 times, and most preferably at least 500 times.

The "amylospheroid" with which the anti-amylospheroid specific antibody of the present invention exhibit high reactivity is a self-assembly of monomeric amyloid β-proteins that has a form of particles. The "form of particles" may be of any particulate form, and examples of the same include granules, fine grains, crystals, and aggregates. A particle diameter is generally about 10 to 20 nm, preferably about 10 to 15 nm, more preferably about 10 to 12 nm, and particularly preferably in the vicinity of about 12 nm. Amylospheroids have a high level activity of inducing neuronal cell death at a protein concentration of about 1 µg/ml or lower, and preferably about 0.45 µg/ml or lower. Amylospheroids having such properties are obtained from a fraction having a glycerol content of about 15% or higher, when fractionated by glycerol density gradient centrifugation.

The reactivity of the anti-amylospheroid specific antibody of the present invention with antigens can be assayed by, for example, a known immunological assay technique such as Western blotting, dot blotting, or ELISA, or election microscopic observation. In such a case, a control amyloid β-protein monomer is a protein composed of about 40 amino acid residues, and it is produced from an amyloid precursor protein (APP) via processing with protease in vivo. A wide variety of such proteins are known to exist, owing to the processing with proteases of various types and the modification made thereafter. Immediately after the secretion, amyloid β40 (Aβ$_{1-40}$: SEQ ID NO: 1) and amyloid β42 (Aβ$_{1-42}$: SEQ ID NO: 2) primarily exist, and further, a minor amount of amyloid β43 (Aβ$_{1-43}$: SEQ ID NO: 3) exists, these amyloids differing from one another in the length of the C-terminal amino acid residues. The amyloid β-protein monomers include any of these proteins. Further, partial polypeptides thereof, and derivatives thereof also are categorized as the amyloid β-protein monomers as well. The term "amyloid β fibrils" refers to fibrillar bodies resulting from self-assembly of amyloid β-proteins, and they have neuronal cell death activity. Such amyloid β fibrils are obtained from organisms or produced by the method described in Lorenzo, A. et al., Proc. Natl. Acad. Sci. U.S.A., 91, 12243-12247, (1994), for example.

According to the third aspect, the anti-amylospheroid specific antibody of the present invention has an activity of inhibiting the neuronal cell death induced by amylospheroids. The term "neuronal cell death induced by amylospheroids" refers to an activity of inducing cell death to neurons that is exhibited by amylospheroids prepared by the aforementioned method or a method described below, and the induced cell death may be apoptosis or necrosis. Neurons are not limited particularly as long as they are neuronal cells, and neuronal cells obtained from mammals (e.g., humans, rats, mice, monkeys, or pigs) may be employed. Neurons induced to differentiate from embryonic stem cells or the like may be used as well. Examples of primary culture cells include cells obtained from the hippocampus, basal forebrain, and cerebral cortex of the aforementioned animals. Examples of primary culture cells also include cells obtained by culturing organs, such as hippocampus, of the aforementioned animals. An anti-amylospheroid specific antibody having such an activity has a higher reactivity with amylospheroids than with amyloid precursor proteins, amyloid β fibrils, or monomeric amyloid β-proteins, for example. Among these, anti-amylospheroid specific antibodies having reactivities with amylospheroids of about 10 to 20 times higher than their reactivities with amyloid precursor proteins are preferably used.

The activity of the anti-amylospheroid specific antibody of the present invention for inhibiting the neuronal cell death induction preferably refers to the aforementioned capacity for completely inhibiting the neuronal cell death induced by amylospheroids. Examples of such an activity, however, may include partial inhibition depending on the antibody dose. A specific method for assaying the inhibitory activity is described below.

It should be noted that examples of the anti-amylospheroid specific antibodies of the present invention include an antibody that has, in addition to any one or more of the first to third aspects, a characteristic of reacting specifically with Alzheimer's disease brains while not exhibiting any significant cross-reactivity with human normal tissues.

Further, examples of the anti-amylospheroid specific antibody of the present invention also include an antibody that has, in addition to any one or more of the first to third aspects, a characteristic of recognizing an epitope specific to a tertiary structure of amylospheroids. Preferred among these is an anti-amylospheroid specific antibody having a characteristic of recognizing an N-terminal of a monomeric amyloid β-protein as an epitope, or a characteristic of not recognizing a primary sequence on the monomeric amyloid β-protein as an epitope. The phrase of "an antibody . . . recognizing an epitope specific to a tertiary structure of amylospheroids" specifically refers to an antibody that can be bound to amylospheroids when the amylospheroids are in a native state, but cannot be bound to amylospheroids when the amylospheroids are in a denatured state.

The following describes in detail a specific method for producing the anti-amylospheroid specific antibody of the present invention, and a method for analyzing the above-described characteristics.

(2) Preparation of Amylospheroids (Antigen)

The antibody of the present invention can be obtained using amylospheroids having the following properties as an antigen. In the present invention, amylospheroids are self assemblies of amyloid β-proteins in the form of particles. The "form of particles" may be of any particulate form, and examples of the same include granules, fine grains, crystals, and aggregates. A particle diameter thereof is generally about 10 to 20 nm, preferably about 10 to 15 nm, more preferably about 10 to 12 nm, and particularly preferably in the vicinity of about 12 nm. Amylospheroids have a high level activity of inducing cell death to neuronal cells at a protein concentration of about 1 μg/ml or lower, and preferably about 0.45 μg/ml or lower. Amylospheroids having such properties are obtained from a fraction having a glycerol content of about 15% or higher, when fractionated by glycerol density gradient centrifugation.

Such amylospheroids can be prepared by first convecting an aqueous solution containing amyloid β-proteins (a first step). In order to prepare a solution efficiently containing amylospheroids, the foregoing convected aqueous solution further is subjected to a process of fractionation to obtain ASPD fraction (a second step). Any of the above amylospheroid-containing solutions can be used as an antigen for preparing the antibody of the present invention.

In the foregoing description, the term "amyloid β-protein" refers to a protein composed of approximately 40 amino acid residues, which is produced from an amyloid precursor protein (APP) via processing with protease in vivo. A wide variety of such proteins are known to exist, owing to the processing with proteases of various types and the modification made thereafter. Immediately after the secretion, amyloid β40 ($A\beta_{1-40}$: SEQ ID NO: 1) and amyloid β42 ($A\beta_{1-42}$: SEQ ID NO: 2) primarily exist, and a minor amount of amyloid β43 ($A\beta_{1-43}$: SEQ ID NO: 3) exists, these amyloids differing from one another in the length of the C-terminal amino acid residues. Amylospheroids are preferably prepared with the use of $A\beta_{X-40}$, $A\beta_{X-42}$, or $A\beta_{X-43}$, which is a full-length molecular species of the amyloid β-protein immediately after the secretion, a mutant thereof, or a derivative thereof, for example. $A\beta_{1-40}$ or $A\beta_{1-42}$ is particularly preferable among them. Any amyloid β-proteins may be used, examples of which include amyloid β-proteins synthesized with the use of a peptide synthesizer, commercialized amyloid β-proteins, or amyloid β-proteins extracted and purified from biological samples. When synthesized peptides are used as amyloid β-proteins, such peptides may be synthesized, extracted, or purified by usually used known techniques. Synthesized peptides may be purified to the extent that a single peak can be obtained by high-performance liquid chromatography. Purification is carried out by, for example, gel filtration or high-performance liquid chromatography. In the present specification, "amyloid β-protein" may be referred to as "amyloid β monomer", "monomeric amyloid β-protein", "Aβ", or "Aβ monomer" in some cases. The thus obtained amyloid β-protein is dissolved in sterile purified water, and the resulting solution is used for preparing an amylospheroid-containing solution, for example. The amount of sterile purified water used for dissolution may be adequately determined, as long as the amyloid β-protein can dissolve therein, and it may be set so that the concentration of an amyloid β-protein in the aqueous solution is preferably about 50 nM to about 2 mM, more preferably about 1 μM to about 1 mM, and further preferably about 50 to about 700 μM. The solution desirably is adjusted to have an adequate salt concentration. A salt concentration may be at any level, as long as the amyloid β-protein can dissolve therein. For example, a final pH level is about 3 to about 11, preferably about 5.5 to about 8.5, and more preferably about 7.5, and a salt concentration is preferably about 1 M or lower. A salt concentration can be adjusted by, for example, adding PBS(−) to an equivalent amount of an aqueous solution of amyloid β-proteins. Amyloid β-proteins may be dissolved by any method without particular limitation, as long as amyloid β-proteins can be completely dissolved in an adequate amount of a solution with an adequate salt concentration.

The first step of a method for preparing an amylospheroid-containing solution is carried out in accordance with a method disclosed in, for example, JP 2001-247600 A. The thus obtained amylospheroid-containing solution, even without any change, has the activity of inducing neuronal cell death and can be used as the antigen of the present invention. The second step of fractionation may be further carried out to obtain a fraction having greater neuronal cell death activity. Fractionation may be carried out in accordance with the method described in JP 2002-105099 A, for example. The thus obtained amylospheroid-containing solution is subjected to a treatment such as concentration if needed and then used as an antigen in the following immunization step.

Amylospheroid formation can be confirmed by the method for analyzing neuronal cell death activity described below, or by determination by means of an electron microscope, for example. Electron microscopic determination may be carried out by any method, as long as the particle diameter of amylospheroids can be analyzed and self assemblies of amylospheroids can be observed without any damage. For example, specifically, distilled water at 30° C. to 40° C. is charged in a petri dish having a diameter of about 18 mm, about 30 μl of a 1.5% (W/V) collodion isoamyl acetate solution is applied dropwise to the surface of the distilled water, and a thin film resulting from solvent evaporation is immediately obtained. This support film is applied to the grid and dried, carbon is deposited in vacuo, and hydrophilicity is imparted to the surface using a glow discharge hydrophilizing apparatus. Subsequently, the grid surface on which the support film has been applied is faced downward, the droplets of the prepared amylospheroid-containing solution is brought into contact therewith, excess moisture is wiped away with filter paper immediately thereafter, and a solution of uranium acetate is added for observation. Electron microscopic observation is preferably carried out as follows with use of an electron microscope at a stabilized high-voltage acceleration of 100 to 120 kV: after the astigmatism is corrected with the use of a grid edge or the like to prevent the sample from being damaged by an electron beam, observation is carried out by a method that reduces damage caused by electron beams, for example.

(3) Preparation of Antibody Using Amylospheroids as Antigen

A method for obtaining the antibody using amylospheroids according to (2) above as an antigen is not particularly limited, as long as with the method it is possible to obtain an antibody having a higher reactivity with amylospheroids than with amyloid precursor proteins, and having any one or more of the following properties:

(i) having a higher reactivity with amylospheroids than with amyloid β fibrils;

(ii) having a higher reactivity with amylospheroids than with monomeric amyloid β-proteins; and (iii) having an activity of inhibiting neuronal cell death induced by amylospheroids. Specifically, a method that is described below in detail is preferable.

As to the antigen, the amylospheroids described in (2) above bound to or polymerized with a protein or a polymer as a carrier, the protein being KLH (keyhole limpet hemocyanin), BSA (bovine serum albumin), OVA (ovalbumin), or the like, are generally used as an immunizing antigen, although a carrier is not necessarily used. An immunizing antigen may be prepared by mixing several types of antigens that have been prepared by different carrier-binding methods.

Animals to be immunized are not particularly limited, and any of the following may be used: rabbits, goats, sheep, hamsters, mice, rats, guinea pigs, chickens, animals other than the humans from which human antibodies can be produced, and the like. It is preferable to use hamsters. Animals are inoculated subcutaneously, intramuscularly, or intraperitoneally with immunizing antigens prepared by thoroughly emulsifying the antigens with the complete or incomplete Freund's adjuvant. Inoculation is carried out every 2 to 5 weeks and continued until the antibody reactivity of the immunized animals with the inoculated antigen is sufficiently elevated. As long as the antibody reactivity of the immunized animals is sufficiently elevated, a dose of the antigen to be inoculated at one time is not particularly limited. Specifically, such a dose is preferably about 1 to about 100 µg. Also, immunization is preferably repeated until the reactivity with amylospheroids of an antibody contained in blood sampled from immunized animals and assayed in the manner described below is found to be higher than that with monomeric amyloid β-proteins. Specifically, immunization is preferably repeated 5 to 20 times.

Blood, ascites, or the like is sampled from the animals 7 to 10 days after the final immunization. Preferably, the immunized animals are exsanguinated, and blood serum is prepared from the blood by centrifugation or other means, for example. The reactivity of the anti-amylospheroid specific antibody of the present invention contained in the blood serum may be analyzed by any method, as long as the reactivity with the amylospheroids prepared in (2) above can be analyzed. For example, amylospheroids are labeled with a fluorescent material, the labeled amylospheroids are allowed to react with the blood serum, and the activity of the labeling agent binding to the antibody is assayed. Specific examples of such a method include electron microscopic observation described above, enzyme immunoassay, such as ELISA, described below, Western blotting, and dot blotting. When the reactivities of the anti-amylospheroid specific antibody of the present invention with amyloid β fibrils are to be assayed and compared, a method by electron microscopic observation is used preferably. When the reactivities thereof with the monomeric amyloid β-proteins and its self-assemblies, amylospheroids, are to be assayed and compared, dot blotting or enzyme immunoassay such as ELISA, is used preferably. The reactivities of antibodies that specifically react with amyloid β fibrils, monomeric amyloid β-proteins, or the partial polypeptides thereof may be compared, so that the anti-amylospheroid specific antibody of the present invention can be selected and obtained therefrom.

Antibodies can be separated and purified by known methods for separating and purifying immunoglobulin. Specific examples of such methods include salting out, alcohol precipitation, isoelectric precipitation, electrophoresis, adsorption on ion exchangers, ultracentrifugation, gel filtration, and selective separation of specific antibodies via adsorption with the aid of an antigen-antibody complex or an active adsorbent.

The thus prepared antibody is a polyclonal antibody, which may be primarily composed of IgG and may contain other immunoglobulins such as IgM or IgA.

On the other hand, when a monoclonal antibody is to be prepared, only amylospheroids as an antigen are usually inoculated intravenously to the animals to be immunized, spleens or lymph nodes that are considered to contain antibody-producing cells are extracted 2 to 5 days, preferably 3 days, thereafter, and the splenic cells or lymph cells are fused with tumor cells. Thereafter, the antibody-producing cells (hybridomas) immortalized via cell fusion are isolated. The tumor cells used herein are desirably of the same species as the splenic cells or lymph cells prepared from the immunized animals, in general. Tumor cells obtained from other animal species may also be used. The immortalization may be carried out by a known method other than the method via cell fusion. For example, it may be carried out by transforming using Epstein-Barr virus (D. Kozbor et al., Eur J Immunol, 14:23 (1984)).

Examples of tumor cells that can be used include myeloma cells, such as p3(p3/x63-Ag8), P3U1, NS-1, MPC-11, SP2/0-Ag14, FO, x63.6.5.3, S194, and R210. Cell fusion may be carried out in accordance with a common technique, such as the method described in, for example, "Monoclonal Antibody Experimentation Manual" (Kodansha Scientific, 1987) or the method described in G. KÖHLER and C. MILSTEIN, Nature, 256, 495, (1975). Cell fusion can be carried out by adding a cell fusion accelerator to a fusion medium comprising the cells of interest suspended therein. Examples of a cell fusion accelerator include hemagglutinating viruses of Japan and polyethylene glycol having an average molecular weight of 1,000 to 6,000. In order to further enhance the fusion efficiency, an auxiliary agent such as dimethyl sulfoxide or cytokine such as IL-6 may be added to a fusion medium. The mixing ratio of the tumor cells to the immunized splenic cells or lymph cells may be approximately 1:1 to 1:10.

Various types of common medium, such as ERDF, RPMI-1640, MEM, or GIT medium, can be used as such a fusion medium. At the time of fusion, blood serum, such as fetal bovine serum (FBS), is preferably removed from the medium, in general. Fusion is carried out by thoroughly mixing predetermined amounts of the immunized splenic cells or lymph cells with tumor cells in the medium, adding a polyethylene glycol solution heated to about 37° C. in advance so that the solution accounts for about 20% to about 50% therein, and allowing these cells to react with each other preferably at 30° C. to 37° C. for about 1 to 10 minutes. Thereafter, a procedure comprising successively adding an adequate medium and performing centrifugation so as to remove the supernatant is repeated.

The hybridomas of interest are cultured in an ordinary selection medium, such as an HAT medium (medium containing hypoxanthine, aminopterin, and thymidine). In the HAT medium, culture may be carried out for a period of time, which is long enough for cells other than the hybridomas of interest (e.g., unfused cells) to die. In general, culture may be continued for several days to several weeks.

The antibodies produced by the resulting hybridomas are contained in the culture supernatant of the hybridomas. The reactivity, reaction specificity, or other properties of the antibodies can be assayed in the same manner as in the case of the method for assaying the aforementioned polyclonal antibody, and hybridomas that produce the anti-amylospheroid specific antibody of the present invention can be obtained selectively.

The obtained hybridomas may be cloned via limiting dilution, whereby hybridoma clones that produce single monoclonal antibodies can be obtained. These hybridoma clones are cultured, either in a medium containing about 1% to about 10% of FBS from which bovine antibodies (IgG) have been removed in advance, or in a serum-free medium, and the resulting culture supernatant is used as a starting material from which monoclonal antibodies of interest are to be obtained by purification. Alternatively, the obtained hybridoma clones may be implanted in the abdominal cavities of the Balb/c or Balb/c (nu/nu) mice to which pristane had been administered in advance, ascites containing monoclonal antibodies at a high concentration is sampled 10 to 14 days thereafter, and the sampled ascites may be used as a starting material from which monoclonal antibodies of interest are to be obtained by purification. Monoclonal antibodies may be purified by conventional methods for purifying immunoglobulin. Examples of such methods include ammonium sulfate fractionation, polyethylene fractionation, ethanol fractionation, anion exchange chromatography, and affinity chromatography involving the use of a column to which protein A, protein G, an anti-mouse immunoglobulin antibodies, or the like has been bound.

The thus obtained anti-amylospheroid specific antibody of the present invention may be used in that state, or it may be used in the form of Fab that is obtained by conventional papain treatment, or in the form of $F(ab')_2$ or Fab' that is obtained by conventional pepsin treatment. Also, examples of the anti-amylospheroid specific antibody of the present invention include a fragment having complementarity-determining regions (CDRs) and hypervariable domains in both variable domains of the heavy chains and the light chains of the antibody, and an antibody prepared by obtaining a gene encoding the fragment by a known technique and further humanizing the same. Further, examples of the anti-amylospheroid specific antibody of the present invention include a fully human antibody prepared via a phage display technique or with the use of a human antibody-producing mouse. Furthermore, the scope of the present invention covers a hybridoma cell line that produces the aforementioned monoclonal antibodies. Examples of the hybridoma of the present invention include hybridomas having accession numbers of FERM BP-10871 and FERM BP-10872 obtained in Examples described later.

An antibody obtained by humanizing a non-human antibody (antibody of mice, rats, hamsters, rabbits, etc.) (hereinafter referred to as a humanized antibody) includes a minimum sequence originating from a non-human immunogloblin, the minimum sequence being a chimera immunogloblin, an immunogloblin chain, or a fragment of the same (e.g., Fv, Fab', $F(ab')_2$, other antigen-binding subsequences of an antibody). The humanized antibody particularly preferably is an antibody partially or entirely composed of amino acid sequences originating from the human antibody germ track, which are obtained by modifying sequences of an antibody having complementarity-determining regions (CDRs) of a non-human antibody. Such a modification is realized by replacing a constant domain of a non-human antibody with a constant domain of a human antibody, and this makes it possible to create a human/non-human chimera having a low enough immunogenicity that it can be used medicinally. More preferably, even a variable domain and a CDR of the antibody are humanized by a technology that has been known in the art by now. A framework region of the variable domain is replaced with a corresponding human framework region, and a non-human CDR either has no substantial change, or is replaced with a sequence originating from its human genome in some cases.

A humanized antibody further refers to an antibody that includes a human framework and at least one non-human antibody-originated CDR and that has a certain constant domain present therein that is substantially identical to a constant domain of a human immunoglobulin. "Substantially identical" means that at least 85 to 100%, and preferably 95 to 100%, of an amino acid sequences is identical. In other words, the present humanized antibody has a configuration in which the entirety except for the CDR portion is identical to a portion corresponding to one or more natural human immunoglobulin sequences.

A humanized antibody has at least three advantageous points as follows, as compared with a non-human antibody and a chimera antibody, in the case where it is used as a pharmaceutical for therapy applied to a human.

1) Since an effector portion of the humanized antibody is human, interaction between it and another factor in the immunoreaction in a human body is excellent. For example, the humanized antibody efficiently destroys target cells owing to its complement-dependent cytotoxicity (CDC) or antibody-dependent cytotoxicity (ADCC).

2) It is considered that the human immune system does not recognize a framework or a constant domain of a humanized antibody as an exogenous matter. Therefore, it is considered that the antigen-antibody reaction in the case where the present humanized antibody is administered to a human body would be lower than that in the case where a non-human antibody or a chimera antibody is administered thereto.

3) It has been reported that a non-human antibody administered has a shorter half-life than that of a human antibody in the human circulatory system. In the case where a humanized antibody is administered, the humanized antibody is expected to have a half-life substantially identical to that of a natural human antibody, which is expected to make it possible to further reduce an amount of the same administered and a frequency of administration of the same.

Methods for humanizing non-human antibodies are know in this art. The humanization is carried out by, for example, the method proposed by Winter et al. (Japanese Patent No. 2912618), the method proposed by Jones et al. (Nature, 321: 522 (1986)), the method proposed by Riechmann et al. (Nature, 332: 323 (1988)), the method proposed by Verhoeyen et al. (Science, 239: 1534 (1988)), the method proposed by Queen et al (Proc. Natl. Acad. Sci. USA 88: 2869 (1991)), or the like. In an operation for obtaining a humanized antibody, it is desirable to cause silent mutation to a codon, for the sake of optimizing the expression of the humanized antibody in a host cell that allows the antibody to be expressed (e.g., the method proposed by Nakamura et al.: Nucleic Acid Res 29: 292 (2000)). The antibody thus obtained, as long as it has specificity described in the present application, is included in the present invention, even if it is a humanized antibody characterized in that it has an amino acid sequence obtained by deletion, replacement, insertion or addition of one or more amino acids in the aforementioned variable domain.

(4) Assay of Reactivity of Anti-Amylospheroid Specific Antibody with Antigen

Hereinafter, examples of specific methods of ELISA and dot blotting for assaying the reactivity of the anti-amylospheroid specific antibody of the present invention with an antigen are provided. Examples of ELISA include solid-phase ELISA and liquid-phase ELISA. The dissociation constant of the anti-amylospheroid specific antibody of the present invention to the antigen may be assayed. The dissociation constant of the antibody can be assayed with the use of an apparatus such as BIACore (manufactured by BIACORE) or via a method in accordance therewith.

(a) Solid-Phase Support Coated with Amylospheroids and Solid-Phase Amylospheroid ELISA With the use of a solid-phase support coated with amylospheroids, a reactivity of the anti-amylospheroid specific antibody with an antigen can be assayed, whereby the anti-amylospheroid specific antibody is detected. Examples of solid-phase supports include spherical, rod-shaped, and plate-shaped supports made of plastic, such as polystyrene or polypropylene, among which a plastic plate support is preferred. The solid-phase support is coated with amylospheroids by conventional techniques, such as adsorption or a method involving the use of a cross-linking agent. From the viewpoint of convenience, physical adsorption of amylospheroids is preferable.

A specific example of an assay technique involving the use of a solid-phase support coated with amylospheroids is amylospheroid ELISA. At the outset, an ELISA plate manufactured by Nunc is coated with amylospheroids prepared in (2) above. In this case, any solvent may be used, as long as the solvent does not allow disassembling of amylospheroids. An example of a preferable solvent is PBS(−). The plate is washed with an adequate solution, such as physiological saline containing a surfactant such as 0.05% Tween 20, blocked with a bovine serum albumin/phosphate buffer (phosphate buffered saline (PBS)) or the like, and then allowed to react with the antibody obtained above. Thereafter, the plate is further washed and then brought into contact with an antibody that reacts with immunoglobulin of the immunized animal as a secondary antibody. After the plate is washed in the same manner, the secondary antibody binding to the plate is detected by using an activity of the labeling material as an indicator. Such an activity of the labeling material can be assayed with the use of, for example, an ELISA plate reader. Further, using amylospheroid ELISA, the antigenic determinant region (epitope) for the anti-amylospheroid specific antibody of the present invention can be determined. Specifically, competitive inhibition of binding between a monomeric amyloid β-protein fragment and the anti-amylospheroid specific antibody may be assayed by amylospheroid ELISA so that the epitope is determined. A plurality of monomeric amyloid β-protein fragments may be used in combination. Further, using amylospheroid ELISA, competitive inhibition of binding between an antigen having a known epitope and the anti-amylospheroid specific antibody may be assayed so that the epitope is determined. It should be noted that the epitope can be determined by the method described in an experimental guidebook such as "Antibodies: A Laboratory Manual" (Ed Harlow et al., Cold Spring Harbor Laboratory (1988)), or a method in accordance therewith.

(b) Liquid-Phase Amylospheroid ELISA

Amylospheroids are allowed to react with a specimen containing an antibody that reacts with amylospheroids, such as a culture supernatant of hybridomas while they are mixed at room temperature for at least 1 hour. A predetermined amount of the mixture is applied to an ELISA plate that has been coated with an adequate amount of rabbit anti-amylospheroid IgG and blocked with, for example, bovine serum albumin/PBS, in advance, and the reaction is allowed to proceed at room temperature for at least 1 hour. Thereafter, the plate is further washed and brought into contact with an antibody that reacts with immunoglobulin in a specimen as a secondary antibody, such as an anti-mouse IgG antibody, anti-mouse IgM, or anti-mouse immunoglobulin. After the plate is washed in the same manner, the secondary antibody binding to the plate is detected by using activity of the labeling material as an indicator. Such an activity of the labeling material can be assayed with the use of, for example, an ELISA plate reader.

(c) Amyloid β Monomer ELISA

The monomeric amyloid β-protein comprising at its N-terminus biotin binding thereto or the monomeric amyloid β-protein comprising at its C terminus biotin binding thereto is mixed with an antibody-containing specimen, such as a culture supernatant of hybridomas, and the mixture is allowed to react at room temperature for at least 1 hour. The mixture is applied to a streptavidin ELISA plate that has been blocked with bovine serum albumin/PBS in advance, and the reaction is allowed to proceed at room temperature for at least 30 minutes. Thereafter, the plate is further washed and then brought into contact with an antibody that reacts with immunoglobulin in the specimen as a secondary antibody, such as an anti-mouse IgG antibody, anti-mouse IgM, or anti-mouse immunoglobulin. After the plate is washed in the same manner, the secondary antibody binding to the plate is detected by using an activity of the labeling material as an indicator. Such an activity of the labeling material can be assayed with the use of, for example, an ELISA plate reader.

(d) Dot Blotting

A specific example of a method of dot blotting for assaying the reactivity of the anti-amylospheroid specific antibody of the present invention with an antigen is described hereinafter. At the outset, an adequate amount of the amylospheroids prepared in (2) above is blotted on a nitrocellulose membrane or the like using a commercially available blotter such as the blotter manufactured by BioRad or the like. In such a case, any solvent can be used, as long as the solvent does not allow disassembling of amylospheroids. For example, PBS(−) is preferably used. In addition to amylospheroids, monomeric amyloid β-proteins, partial peptides thereof, or only a solvent may be preferably blotted as the control examples. The membrane is washed with an adequate buffer, such as a phosphate buffer (phosphate buffered saline (PBS)), blocked with skim milk/TTBS (Tween-Tris buffered saline) or the like, brought into contact with the antibody obtained above, further washed with TTBS or the like, brought into contact with an antibody that reacts with immunoglobulin of the immunized animal as a secondary antibody, and washed in the same manner. Thereafter, the secondary antibody binding to the membrane is detected by using the activity of the labeling material or the like as an indicator. As the control, an antibody that reacts with the monomeric amyloid β-proteins is preferably used. An example of such antibody is 6E10 (produced by Senetek).

(5) Analysis of Activity for Inhibiting Neuronal Cell Death Induced by Amylospheroids An example of a method for analyzing the activity of the anti-amylospheroid specific antibody of the present invention for inhibiting neuronal cell death induced by amylospheroids (hereinafter such an activity may be referred to as "activity of neutralizing neuronal cytotoxicity" or "activity of inhibiting the neuronal cell death induction" in some cases) is provided below.

At the outset, the neuronal cell death induction with the use of amylospheroids can be carried out by adding the amylospheroids to a culture solution of neuronal cells and culturing the same in accordance with a conventional technique. Whether or not the anti-amylospheroid specific antibody of the present invention has the activity of neutralizing neuronal cytotoxicity can be analyzed in the following manner: the neurons and amylospheroids are cultured in the presence of the anti-amylospheroid specific antibody, and whether neuronal cell death is induced or not is checked. Cell death induced by amylospheroids may be apoptosis or necrosis. Cells used are not particularly limited as long as they are neuronal cells, and neuronal cells obtained from mammals (e.g., humans, rats, mice, monkeys, or pigs) are preferable. Primary culture cells are also preferable. Examples of primary culture cells include cells obtained from the hippocampus, basal forebrain, and cerebral cortex of the aforementioned animals. Alternatively, cells obtained by culturing organs, such as hippocampus, of the aforementioned animals may be used. Neurons induced to differentiate from ES cells or the like may also be used.

These cells or organs can be cultured in accordance with a conventional technique. Specifically, primary culture of neuronal cells and culture of established neuronal cell lines can be carried out in accordance with methods described in, for example, Hoshi, M. et al., Proc. Natl. Acad. Sci. U.S.A., 93, 2719-2723, (1996) or Schubert, D. et al., Nature, 249 (454), 224-227, (1974). Organ culture can be carried out in accordance with the method described in, for example, Gary Banker and Kimbery Goslin, Culturing Nerve Cells, 2nd Edition, MIT Press, Cambridge, (1998). The amount of amylospheroids to be added, in order to induce cell death to the thus cultured neuronal cells and organs, can be adequately selected. In general, amylospheroids are capable of inducing cell death at a concentration substantially equivalent to that of toxic amyloid β-proteins that exist in the brains of patients with Alzheimer's disease or the like. For example, the amylospheroids obtained in (2) above are capable of inducing cell death to the primary culture cells at an amyloid β-protein concentration of about 1 µg/ml or lower and preferably about 0.45 g/ml or lower, in the culture solution, as described above. It should be noted that this is presented for an illustrative purpose, and the concentration is not limited to the above-described range.

The amount of the anti-amylospheroid specific antibody of the present invention in the culture solution is adequately selected in accordance with the reactivity of the antibody with the antigen. Specifically, such an amount is preferably between about 0.0001 mg/ml and about 1 mg/ml, for example. The timing of adding the anti-amylospheroid specific antibody to the culture solution is not particularly limited, as long as the activity of neutralizing neuronal cytotoxicity can be confirmed. However, since neuronal cell death is induced by amylospheroids about 6 hours after the culture, the anti-amylospheroid specific antibody is added prior to the culture, preferably at the initial stage of culture. Further, amylospheroids and the anti-amylospheroid specific antibody are incubated in another container, and then added to the above-described culture solution. As the control, an antibody that does not react with amylospheroids or an antibody having so low a reactivity with amylospheroids that the reactivity does not affect the induction of neuronal cell death, is used preferably. For example, an antibody that reacts with the monomeric amyloid β-proteins is preferably used, and a specific example thereof is 6E10 (produced by Senetek).

In general, neuronal cell death induced by amylospheroids starts occurring about 6 hours after the addition of an effective amount of amylospheroids. Significant cell death can be observed about 48 hours after the addition. In this analytical method, accordingly, induction of neuronal cell death is preferably assayed about 20 hours after the initiation of culture; however, such timing is adequately selected in accordance with the cell death activity system of amylospheroids used.

The neuronal cell death activity can be assayed by common techniques for detecting cell death. Specific examples of such techniques include MTT activity assay (Mossman, T., J. Immunol. Methods, 65, 55, (1983)), propidium iodide staining (Ankarcrona, M. et al., Neuron, 15, 961, (1995)), trypan blue dye exclusion (Woo, K. B., Funkhouser, W. K, Sullivan, C., and Alabaster, O., Cell Tissue Kinet., 13 (6), 591-604, (1980)), TUNEL, and ELISA that detects fragmented DNA (Roche). Staining with propidium iodide or the like and ELISA that detects fragmented DNA are particularly preferable. Staining with propidium iodide or the like may be monostaining only with propidium iodide that selectively stains dead cells. Alternatively, propidium iodide staining may be carried out in combination with a plurality of other dyes. Specifically, dyes that can be preferably used in combination include calcein-AM (manufactured by Molecular Probes) that selectively stains living cells, Hoechst 33258 (H33258: Bisbenzimide H33258) that stains any cells, and the like.

The activity of the anti-amylospheroid specific antibody of the present invention for inhibiting induction of neuronal cell death can be analyzed by directly administering the anti-amylospheroid specific antibody of the present invention to an individual animal Cell death induced by amylospheroids may be apoptosis or necrosis. Animals to be used are not particularly limited, as long as the animals have neuronal cells, such as mammalian animals (mice, rats, and primates). Preferably, animal models of Alzheimer's disease in which neuronal cell death has particularly occurred are used. As to the administration method, in addition to direct administration to a site where neuronal cells exist such as the brain, conventional methods for administering pharmaceuticals can be employed, such as oral administration, intravenous injection, and intraperitoneal administration. Specific examples of such direct administration to a site where neuronal cells exist such as the brain include a method wherein the anti-amylospheroid specific antibody of the present invention is administered intraventricularly in the vicinity of the target site using an osmotic pump or via microfusion into the brain parenchyma at the target site using a micropipette or the like, in the case of the brain tissue of a rat, a mouse, or another animal. After the administration had been continued for a given period of time, changes in the brain function are assayed via PET/MRI, tissue around the site of administration is immediately taken out, and tissue slices are prepared, so that it can be checked whether or not neuronal cell death has occurred. The occurrence of neuronal cell death can be detected by histological staining, Western blotting, or the like. Histological staining can be carried out by, for example, TUNEL staining or immunostaining with the use of an anti-caspase antibody or the like.

(6) Method for Screening a Therapeutic and/or Preventive Agent for Alzheimer's Disease Amylospheroids, when added to cultured neuronal cells, can induce said cells to die. Therefore, amylospheroids, which are self-assemblies of amyloid β-proteins, is considered to induce neurodegeneration in Alzheimer's disease in the same manner.

The anti-amylospheroid specific antibody of the present invention exhibits a high reactivity with amylospheroids, and has an activity of inhibiting the neuronal cell death induced by amylospheroids. Thus, the screening of a therapeutic and/or preventive agent for Alzheimer's disease can be performed by binding examined substances to amylospheroids in competition with the anti-amylospheroid specific antibody of the present invention and selecting substances using their reactivities as indicators. The anti-amylospheroid specific antibody of the present invention per se can be an active ingredient of a therapeutic and/or preventive agent for Alzheimer's disease. In other words, the anti-amylospheroid specific antibody of the present invention exhibits a low reactivity with respect to amyloid precursor proteins, amyloid β monomers, and other structures formed with these, and has a high specificity with respect to brains; for this reason, the antibody of the present invention could be a therapeutic agent for Alzheimer disease with higher safety, as compared with conventional anti-amylospheroid antibodies disclosed by WO 2006/016644.

A specific example of a method for screening examined substances is described hereinafter. Examples of examined substances include peptides, proteins, nonpeptidic compounds, synthetic compounds, fermentation products, cell extracts, plant extracts, and animal tissue extracts. Such compounds may be novel or known compounds. Reactivity with amylospheroids is assayed by the method for analyzing the reactivity between the anti-amylospheroid specific antibody and amylospheroids described in (4) above, wherein the examined substance is added to the reaction solution. The amounts of amylospheroids, the anti-amylospheroid specific antibody, and the examined substance to be mixed can be selected so that an appropriate concentration is obtained.

The examined substance is preferably labeled with a labeling material. Through this analysis, it can be determined that a substance that has been bound to amylospheroids can be used as an active ingredient of a therapeutic and/or preventive agent for Alzheimer's disease. Preferably, the selected substance is used instead of the anti-amylospheroid specific antibody used in the method described in (5) above to examine whether or not the substance inhibits the neuronal cell death induced by amylospheroids.

The thus selected substance and the anti-amylospheroid specific antibody of the present invention per se are useful as active ingredients of medicine for preventing and/or treating Alzheimer's disease, and they may be formed into physiologically acceptable salts thereof, hydrates, solvates, and the like. Those to which metal ions such as Fe or Zn ions, sugar chains, or glycoproteins have been added are also preferable. Examples of physiologically acceptable salts include: mineral acid salts, such as hydrochloride and sulfate; organic acid salts, such as citrate, oxalate, and p-toluenesulfonate; and amino acid salts, such as glycine. The anti-amylospheroid specific antibody of a humanized type or a fully human antibody type obtained by the modification by the aforementioned method is preferably used. Modification of an antibody into a form suitable for administration to humans may be carried out via several known techniques in adequate combination.

The medicine provided by the present invention comprises, as active ingredients, either substances that have been determined to have an activity of inhibiting neuronal cell death by the screening method of the present invention, or the anti-amylospheroid specific antibody of the present invention, and such medicine can be used as a medicine for preventing and/or treating Alzheimer's disease. Substances that have been determined to have an activity of inhibiting neuronal cell death by the screening method of the present invention and the anti-amylospheroid specific antibodies per se may be administered to a patient as a medicine. In general, a pharmaceutical composition comprising one, two, or more of such active ingredients is preferably prepared and administered to a patient. Examples of such pharmaceutical compositions include: oral preparations, such as tablets, capsules, granules, fine grains, powders, pills, troches, sublingual agents, and liquids; and parenteral preparations, such as injections, suppositories, ointments, and adhesive preparations.

Tablets or capsules for oral administration are generally provided in unit dosage forms, and such dosage forms can be produced with the addition of common pharmaceutical carriers, such as binders, fillers, diluents, tableting agents, lubricants, disintegrators, colorants, flavoring agents, or moistening agents. Tablets can be coated with, for example, an enteric coating agent in accordance with a method well known in the art. Tablets can be produced with the use of, for example, fillers, disintegrators, lubricants, or moistening agents.

Liquid preparations for oral administration are provided in the form of aqueous or oil suspensions, solutions, emulsions, syrups, or elixirs. Also, liquid preparations are provided in the form of dry preparation to be redissolved in water or adequate vehicle before use. Common additives, such as suspending agents, emulsifiers, preservatives, and, if needed, common flavoring agents or colorants, can be added to such liquid preparations.

Preparations for oral administration can be produced by a method well known in the art, such as mixing, filling, or tableting. Also, active ingredients may be distributed in preparations using a large quantity of fillers or the like through iterative compounding. Preparations for parenteral administration are generally provided in the form of liquid carrier-mediated preparations containing substances as active ingredients as well as sterile vehicles. Solvents for parenteral administration are generally produced by dissolving substances, as active ingredients, in a vehicle, subjecting the resulting solution to sterilization filtration, and filling the filtrate in an adequate vial or ampule, followed by sealing. In order to enhance stability, the composition may be frozen and filled in a vial, and thereafter moisture may be removed in vacuo. Parenteral suspensions are produced in substantially the same manner as with the case of parenteral liquids. Parenteral suspensions are preferably produced by suspending active ingredients in a vehicle and sterilizing the suspension by ethylene oxide or the like. Further, surfactants, moistening agents, or the like may be added as required in order to evenly distribute active ingredients.

A dose of a substance as an active ingredient is adequately determined in accordance with the following, for example: the activity level of the substance; the purpose of treatment or prevention; and symptoms, body weight, age, and sex of a patient. Desirably, administration is carried out once or several separate times per day. When the anti-amylospheroid specific antibody of the present invention is an active ingredient, for example, a dose thereof is generally about 1 μg to about 100 mg, and preferably about 10 μg to about 50 mg, per 1 kg of the body weight in a single administration.

(7) Method for Detecting Individual with Alzheimer's Disease Using Anti-Amylospheroid Specific Antibody, and Detection Reagent Since amylospheroids, when added to cultured neuronal cells, can induce such cells to die, the amylospheroids, a self-assembly of monomeric amyloid β-proteins, is considered to induce neurodegeneration in Alzheimer's disease as well. The anti-amylospheroid specific antibody of the present invention has a high reactivity with these amylospheroids. Thus, individuals with Alzheimer's disease can be identified by detecting amylospheroids in biological samples using this antibody.

Examples of biological samples include body fluid, such as blood, cerebrospinal fluid, and urine, obtained from an individual suspected of Alzheimer's disease, and among them, blood is particularly preferable. A sample can be obtained by, for example, in the case of blood, sampling blood from the cubital vein of an individual suspected of Alzheimer's disease using a blood-sampling tube, and separating blood plasma or serum via centrifugation or the like. A cerebrospinal fluid sample can be obtained by, for example, sampling cerebral fluid from an individual suspected of Alzheimer's disease via lumbar puncture under anesthesia, and subjecting the sample to centrifugation. In order to prevent amylospheroids from denaturation or blood from coagulation in the obtained biological sample, an enzyme inhibitor is preferably added to the biological sample at the time of or after sampling. As an enzyme inhibitor, a protease inhibitor is used, examples of which include aprotinin, antipain, pepstatin, leupeptin, EGTA, PMSF (phenylmethanesulfonyl fluoride), or TLCK (tosyllysine chloromethyl ketone). The obtained biological samples may be subjected to concentration or other processing if needed, so that the sensitivity for detecting amylospheroids can be increased.

Detection of amylospheroids in biological samples using the anti-amylospheroid specific antibody can be carried out via conventional immunological assay techniques. Specific examples of such techniques include sandwich assay, competitive assay, immunometric assay, and nephelometry. In the sandwich assay, biological samples are brought into contact with the anti-amylospheroid specific antibody of the present invention bound to a solid-phase, the labeled anti-amylospheroid specific antibody is allowed to react therewith, and a signal of a labeling material binding to the solid-phase is assayed. Thus, the amylospheroid level in the biological samples can be assayed. When the amylospheroid level in the biological samples is assayed by such immunological assay, such level is preferably determined based on the standard curve prepared using a standard solution containing a known amount of amylospheroids. Specifically, immunological assay can be carried out in accordance with experimental guidebooks, such as Seikagaku Jikkenhou 11, "Enzyme Immunoassay" (Tijssen, P., Tokyo Kagaku Dojin, Co., Ltd.) or "Antibodies: A Laboratory Manual" (Ed Harlow et al, Cold Spring Harbor Laboratory, (1988)). Several assay techniques can be carried out in adequate combination. The scope of the present invention also covers a reagent comprising the anti-amylospheroid specific antibody for detecting individuals with Alzheimer's disease, used for such assay techniques.

EXAMPLES

The present invention is hereinafter described with reference to examples, though the present invention is not limited to these examples at all. In the following examples and in this description, "PBS" refers to phosphate buffered saline, "TTBS" refers to Tween-Tris buffered saline, and "HRP" refers to horseradish peroxidase.

Example 1

Preparation of Amylospheroid-Containing Solution (1) Production of Amyloid β40 (SEQ ID NO: 1) Resin 342 mg of Fmoc-Val resin (amine content: 0.73 mmol/g of resin) was mounted on an A433 automated peptide synthesizer (Perkin Elmer Applied Biosystems). Applied to this were Fmoc-Val-OH, Fmoc-Gly-OH, Fmoc-Gly-OH, Fmoc-Val-OH, Fmoc-Met-OH, Fmoc-Leu-OH, Fmoc-Gly-OH, Fmoc-Ile-OH, Fmoc-Ile-OH, Fmoc-Ala-OH, Fmoc-Gly-OH, Fmoc-Lys(Boc)-OH, Fmoc-Asn(Trt)-OH, Fmoc-Ser(tBu)-OH, Fmoc-Gly-OH, Fmoc-Val-OH, Fmoc-Asp(OtBu)-OH, Fmoc-Glu(OtBu)-OH, Fmoc-Ala-OH, Fmoc-Phe-OH, Fmoc-Phe-OH, Fmoc-Val-OH, Fmoc-Leu-OH, Fmoc-Lys(Boc)-OH, Fmoc-Gln(Trt)-OH, Fmoc-His(Trt)-OH, Fmoc-His(Trt)-OH, Fmoc-Val-OH, Fmoc-Glu(OtBu)-OH, Fmoc-Tyr(tBu)-OH, Fmoc-Gly-OH, Fmoc-Ser(tBu)-OH, Fmoc-Asp(OtBu)-OH, Fmoc-His(Trt)-OH, Fmoc-Arg(Pmc)-OH, Fmoc-Phe-OH, Fmoc-Glu(OtBu)-OH, Fmoc-Ala-OH, and Fmoc-Asp(OtBu)-OH, and these were successively condensed using HBTU[2-(1H-benzotriazol-1-yl)-1,1,3,3-tetramethyluronium hexafluorophosphate] as a condensation agent, whereby 1.515 g of side-chain protected amyloid β40 resin was obtained.

(2) Treatment with Trifluoroacetic Acid 304 mg of a resin fraction was sampled from the side-chain protected amyloid β40 resin obtained in (1) above, and 0.75 ml of phenol, 0.5 ml of thioanisole, 8.25 ml of trifluoroacetic acid, 0.25 ml of ethanedithiol, and 0.5 ml of distilled water were added thereto. The reaction was allowed to proceed under ice cooling for 5 minutes and then at room temperature for 1.5 hours. After the completion of the reaction, 200 ml of ice-cooled diethyl ether was added to cause peptide to precipitate. All of the contents were filtered through a glass filter, the filtrate was washed with cold diethyl ether, and extraction was carried out using about 200 ml of 0.1% trifluoroacetic acid containing 35% of acetonitrile, whereby 191 mg of a crude peptide represented as follows was obtained:

H-Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly-Val-Val-OH.

(3) Purification of Peptide

This crude peptide was dissolved in 40 ml of 0.1% trifluoroacetic acid containing 35% of acetonitrile, and then was purified by HPLC using a reverse phase column (inner diameter: 2 cm; length: 25 cm) containing ODS (octadecylsilane) bound to silica. Elution was carried out by linearly raising an acetonitrile content from 22% to 42% in 0.1% trifluoroacetic acid over the period of 20 minutes. The yield of the purification product was 35 mg. The structure of this substance was examined by the MALDI-TOF mass analysis. The measured value was [M+H]+4330.99, and the calculated value was $(C_{194}H_{295}N_{53}O_{58}S_1+H)$4330.89. Amyloid β42 synthesized and produced in accordance with the aforementioned method and amyloid β42 purchased from Bachem were subjected to the following experiment.

(4) Preparation of Amylospheroid-Containing Solution 10 nmol of the amyloid β40 purified in (3) above was charged in a 1.5-ml eppendorf tube, and 500 μl of ultrapure water and 500 μl of Dulbecco's phosphate buffer(−) (Nippon Suisan Kaisha, Ltd., hereinafter referred to as PBS(−)) were successively added in that order so that amyloid β-proteins were completely dissolved. The eppendorf tube containing this aqueous amyloid β-protein solution was mounted on a Duck rotor (TAITEC, rotor: RT50) and rotated at 37° C. at 35 rpm for 7 days, so that amylospheroid 40 was prepared. Amyloid β42 (either purified in (3) above or produced by Bachem) was also rotated for about 10 hours in accordance with the above-mentioned method, whereby amylospheroid 42 was prepared.

Example 2

Preparation of Hamster Monoclonal Anti-Amylospheroid Specific Antibody

Amylospheroid 42 prepared in PBS was mixed with the equivalent amount of the complete Freund's adjuvant (WAKO) and the mixture was emulsified. 0.2 ml of the resultant mixture was administered subcutaneously in the backs of Armenian hamsters for immunization (16 µg/0.2 ml/hamster). Amylospheroids emulsified with the incomplete Freund's adjuvant (Sigma-Aldrich) was also administered in the same manner every two weeks. After 5 immunization procedures, blood was sampled from carotid artery so that blood plasma was prepared. The blood plasma was serially diluted in a 1% bovine serum albumin (BSA, fraction V; Sigma-Aldrich) solution (in PBS(−)), and the reactivity of the anti-amylospheroid specific antibody with amylospheroids was assayed by the following solid-phase amylospheroid ELISA.

To individuals that had become to exhibit sufficiently improved reactivity as a result of 6 to 12 immunization procedures, 16 µg of amylospheroids (in 0.2 ml of PBS(−)) was administered intraperitoneally at last for boosting. Splenic cells were collected 3 days after the boosting and were fused with mouse myeloma cells (SP2/0-Ag14), the number of which was a half that of the splenic cells, by a conventional technique involving the use of polyethylene glycol 4000. The fused cells were suspended in GIT medium (WAKO) containing 10% of fetal bovine serum, 10% of BM condimed H-1 (Roche Diagnostics), and HAT (Sigma-Aldrich), and the cell suspension was plated onto a 96-well plate (FALCON), so that each well contained $5 \times 10^4$ myeloma cells/0.1 ml of the culture solution. The culture solution was added 3 days later, the culture solution was exchanged 7 days later, culture was continued for additional 2 to 3 days, and the supernatant was collected. The anti-amylospheroid specific antibodies in the supernatant were analyzed by ELISA described below, and cells producing specific antibodies were expanded on a 24-well plate (IWAKI). When cloning was carried out via limiting dilution, hybridomas were plated onto a 96-well plate so that each well contained 200 µl of the culture solution having 0.3 cell/well, and culture was continued with a half of the culture solution being exchanged once a week.

Antibodies obtained from Hybridomas H3-17-2-2 (Hybridoma haASD1), H5-3-2-45 (Hybridoma haASD2), H5-24-7, H-5-47-10, and H4-3-5-4 for producing hamster monoclonal antibodies are referred to as "haASD1", "haASD2", "haASD3", "haASD4", and "haASD5", respectively.

Hybridomas haASD1 and haASD2 were deposited at the International Patent Organism Depositary of the National Institute of Advanced Industrial Science and Technology (Tsukuba Central 6, 1-1-1 Higashi, Tsukuba, Ibaraki, Japan) as of Jul. 13, 2007 under the accession numbers of FERM BP-10871 and FERM BP-10872, respectively.

Antibodies were separated from hybridomas H3-17-2-2, H5-3-2-45, H5-24-7, H5-47-10, and H4-3-5-4 and purified in the following manner. Hybridomas were cultured in about 1 L of CD Hybridoma medium (Invitrogen) for 1 week, and the culture supernatant was collected via centrifugation. The collected supernatant was filtered through a 0.45 µm filter, and the filtrate was added to 2 ml of protein-A sepharose equilibrated with PBS(−), and IgG antibodies were separated and purified in the same manner as in Example 2 (1) disclosed in WO 2006/016644.

Example 3

Analysis of Antibody Properties (1) Solid-Phase Amylospheroid ELISA (Analysis of Reactivity with Amylospheroids)

50 µl of amylospheroids 42 diluted to 1 µg/ml in 1/2-concentration PBS(−) was applied to a 96-well ELISA plate (MaxiSorp, Nunc), and the plate was subjected to overnight coating at 4° C. A 1% bovine serum albumin (BSA, fraction V; Sigma-Aldrich) solution (in PBS(−)) was added thereto at room temperature over the period of at least 1 hour so that non-specific binding sites were blocked, and the plate was washed with water. 50 µl of anti-serum or hybridoma culture supernatant diluted in a 1% bovine serum albumin solution (in PBS(−)) was added and the reaction was allowed to proceed at room temperature for at least 1 hour. The plate was washed five times with 0.05% Tween 20-containing physiological saline, a peroxidase-labeled secondary antibody diluted to 1 µg/ml (anti-hamster IgG antibodies (ROCKLAND) was also added thereto, and the reaction was allowed to proceed at room temperature for 1 hour. After the plate was washed five times, a substrate solution was added to cause a coloring reaction for a predetermined period of time, and the absorbance was assayed using a plate reader.

Representative examples of results of the hamster monoclonal antibodies established in Example 2 are shown in FIG. 1. The antibodies established in Example 2 exhibited a strong reactivity with amylospheroids at a low concentration.

(2) Dot Blot Analysis (Analysis of Reactivity with Amylospheroids, Amyloid β Fibril, Amyloid β Monomer, and Amyloid Precursor Protein)

With the use of a blotter (BioRad), a solution containing monomeric amyloid β40 or β42-protein and amylospheroid 40 or 42 prepared in Example 1 dissolved in 1,1,1,3,3,3-hexafluoro-2-propanol (Sigma-Aldrich) as a solvent, as well as 5 ng each of Aβ fibrils prepared from amyloid β40 and commercially available amyloid precursor protein sAPPα (Sigma) were blotted on nitrocellulose membranes (Schleicher & Schuell, 0.2µ). These membranes were washed with PBS(−), and thereafter, they were removed from the blotter.

After the protein-blotted membranes were blocked with 5% skim milk/0.05% TTBS for 1 hour, the membranes were soaked in rabbit polyclonal anti-amylospheroid specific antibodies (rpASD1, rpASD2, rpASD3) (0.01 µg/mL), mouse monoclonal anti-amylospheroid antibody (mASD3) (0.05 µg/mL), and the antibody haASD1 obtained in Example 2 (0.01 µg/mL), and the reaction was allowed to proceed in a wet box overnight at 4° C. Thereafter, the membranes were washed with 0.05% TTBS, and were allowed to react with anti-rabbit IgG, anti-mouse IgG, or anti-hamster IgG to which 0.05 to 1 µg/ml of horseradish-derived peroxidase was binding as secondary antibodies for 1 hour. Thereafter, the membranes were washed with 0.05% TTBS so that unreacted secondary antibodies were removed, and the membranes were soaked in SuperSignal West-Femto (Pierce), subjected to incubation for 5 minutes. Thereafter, chemiluminescent signals were detected and image data were imported using an image analyzer, LAS-1000 plus (Fuji Photo Film Co., Ltd.). Employed as the control for inspecting the antibody reactivity were those in which 0.5 µg/ml of anti-amyloid β antibody "6E10" (Senetek) and 0.04 µg/mL of anti-APP N-terminal antibody "22C11" (Chemicon) were used as the primary antibody.

The results are shown in FIG. 2.

In FIG. 2, dots of "Aβ1-40" and "Aβ1-42" represent the results as to a monomer; an amylospheroid 40-containing solution prepared in Example 1; a fraction of the same retained by 100 kDa ultrafilter membrane; an amylospheroid 42-containing solution; and a fraction of the same retained by 100 kDa ultrafilter membrane. Dots of "fibril" represent the results as to Aβ fibril prepared from Aβ1-40, and dots of "sAPPα" represent the results as to a commercially available amyloid precursor protein (Sigma). The following was found: commercially available anti-amyloid β antibody "6E10" reacted with any of the amylospheroid 40 and amylospheroid 42 prepared in Example 1, monomer, fibril, and sAPPα protein; on the other hand, the hamster monoclonal antibody (haASD1) established in Example 2 selectively highly reacted with amylospheroid 40 and amylospheroid 42, while exhibiting no reactivity with amyloid precursor protein sAPPα at all.

(3) Measurement of Dissociation Constant

10 μg/ml amylospheroid (42ASPD), amyloid β monomer (42Aβ, 40Aβ), and Aβ fibril (fibril) prepared from 40Aβ were coupled to CM5 sensor chips of BIACore 3000 (BIAcore) at a concentration of 10 g/ml in 50 mM acetate buffer. With the use of an antibody solution subjected to two-fold serial dilution from the maximal concentration of 100 nM in a buffer (10 mM HEPES, pH 7.4, 0.15 M NaCl, 3 mM EDTA, 0.005% Surfactant P20), the association rate constant and the dissociation rate constant were determined. With the use of these constants, the dissociation constant was calculated by the following equation.

Dissociation constant=dissociation rate constant/association rate constant

Table 1 shows the dissociation constants (Kd) of mouse monoclonal anti-amylospheroid antibodies, hamster monoclonal anti-amylospheroid specific antibodies, and commercially available antibody (6E 10) with respect to amylospheroids.

The hamster monoclonal anti-amylospheroid specific antibodies had a strong affinity (Kd $10^{-11}$ to $10^{-9}$ M) with ASPD, and exhibited a higher (1 to 2 orders) selectivity than with the amyloid β monomer or fibril, like the mouse monoclonal anti-amylospheroid antibodies.

TABLE 1

Dissociation constants of anti-amylospheroid antibodies

| Antibody | Affinity, KD (nM) | | | |
|---|---|---|---|---|
| | 42ASPD | 42Aβ | 40Aβ | fibril |
| mASD1 | 0.19 | 1.2 | 8.1 | 1.61 |
| mASD3 | 0.036 | 1.0 | 2.6 | 0.35 |
| haASD1 | 0.49 | 2.4 | 44.6 | 8.49 |
| haASD2 | 0.002 | 0.97 | 7.6 | 0.87 |
| 6E10 | 18.3 | 17.2 | 37.3 | 1.33 |

Example 4

Determination of Antigenic Determinant Region (Epitope) of Anti-Amylospheroid Antibody (1) Antigenic Determinant Region (Epitope) of Anti-Amylospheroid Antibody In order to determine the epitope of the anti-amylospheroid antibody, fragments each comprising 5 residues starting from the N-terminus of a partial sequence of the monomeric amyloid β-protein were successively subjected to chemical synthesis, whereby 38 different types of partial sequences of peptides comprising amyloid β5 residues (hereafter abbreviated as "Aβ," and referred to as Aβ1-5, Aβ2-6, Aβ3-7, . . . Aβ38-42 in order from the N-terminus) were obtained. Each of the Aβs was purified by HPLC until a single peak was obtained, a predetermined amount of each was lyophilized, and the product was stored at −20° C. until just before use.

Each of the above Aβs was dissolved in sterile 0.5×PBS(−), and a Aβ-antibody mixed solution was prepared so as to contain each Aβ in amounts 100 to 1,000,000 times larger than the amount of IgG-purified anti-amylospheroid antibody (by molar ratio). The Aβ diluents were applied to the amylospheroid 40 solid-phase plate prepared in Example 3(1), the plate was subjected to shaking at 4° C. overnight, the plate was washed with a 0.01% Tween 20-PBS(−) solution, and 1/10,000-fold diluted secondary antibody (anti-rabbit antibody in the case of polyclonal antibodies and anti-mouse antibody or anti-hamster antibody in the case of monoclonal antibodies) to which peroxidase had been bound were added, followed by shaking for 1 hour. The resultant was washed with a 0.01% Tween 20-PBS(−) solution, and a coloring reaction was performed using a TMB substrate kit (Pierce). After the termination of the coloring reaction, the absorbance at 450 nm was measured using a plate reader (Benchmark; BioRad).

The results are shown in FIG. 3. According to this, haASD2 and the commercially available antibody 82E1 (IBL (Immuno-Biological Laboratories Co., Ltd.)) were found to be competitively inhibited, most potently by N-terminus peptide (Aβ1-5) of the monomeric amyloid β-protein. On the other hand, haASD1 and haASD3 were not competitively inhibited by any one of amyloid β 5-residue partial sequence peptides (even though the Aβ mixture ratio by mole with respect to antibodies was raised to 1,000,000 folds). This clearly suggests that the epitope recognized by the anti-amylospheroid specific antibody of the present invention is different from epitopes recognized by the conventionally-known antibodies, and the anti-amylospheroid specific antibody of the present invention recognizes an epitope specific to a tertiary structure of ASPD.

Example 5

Evaluation of Activity of Neutralizing Cytotoxicity of Amylospheroids (1) Neutralization of Amylospheroid Toxicity by Monoclonal Anti-Amylospheroid Antibody An activity of neutralizing amylospheroid toxicity was evaluated using each of the monoclonal anti-amylospheroid antibodies obtained in Example 2. For evaluation, rat hippocampus primary culture neurons were used. The primary culture of hippocampus was prepared basically in the same manner as in the case of the basal forebrain in Example 5 disclosed in WO 2006/016644, but the plating was performed so that the culture density was $1.0 \times 10^5$ cells/cm$^2$. As amylospheroids, the amylospheroid 42 prepared by the method of Example 1 was used. The experiment conditions were as follows:

Concentration of amylospheroid 42: 1.25 μM
Period for exposure to amylospheroids: 45 hours
Cell: rat hippocampus neurons
Detected by PI staining The monoclonal anti-amylospheroid antibody haASD2 exhibited an effect of neutralizing neurotoxicity of amylospheroids with respect to the hippocampus primary culture neurons as well. As shown in FIG. 4, haASD2 exhibited a concentration-dependent neutralizing activity to neurotoxicity of amylospheroids (concentration: 5 to 50 μg/ml).

Example 6

Reactivity with Amyloid Precursor Protein (1) Western Blotting

Western blotting was performed using brain extracts sampled from Tg2576 mice that are model animals of Alzheimer's disease and have excessive expression of human APP (hAPP) (Science 1996 Oct. 4; 274 (5284): 99-102), and reactivities of the ASPD antibodies and 6E10 were examined. Specifically, TBS (tris buffered saline)-soluble fractions of cerebral cortex and hippocampus of Tg2576 mice (15 months old) were treated with NuPAGE LDS sample buffer, samples of about 50 µg each were applied to NuPAGE Novex Bis-Tris Gel (4-12%), and subjected to electrophoresis (200 V). Thereafter, the samples was transferred to nitrocellulose membranes (30 V, 60 minutes), and the membranes having the samples transferred thereto were blocked with TTBS (TBS containing 0.05% of Tween 20) containing 5% of skim milk (room temperature, 2 hours). Then, the reaction of the samples of the membranes with each antibody (1 µg/ml) diluted with the same solution was allowed to proceed (4° C., overnight), and after the membranes were washed, the detection was performed with use of 1-HRP-labeled secondary antibody (SuperFemto).

As a result, in the samples of Tg2576 mice, 6E10 reacted with Aβ monomer and hAPP (FIG. 5, bands indicated as "Aβ monomer" and "APP", respectively); and the mouse ASPD monoclonal antibodies (mASD1, mASD2, mASD3) disclosed in WO 2006/016644 did not react with Aβ monomer, but reacted with hAPP (FIG. 6, bands indicated by arrows). On the other hand, the hamster ASPD monoclonal antibodies of the present invention did not exhibit reactivities with Aβ monomer and hAPP as the reactivities exhibited by 6E10 or mouse antibodies (FIG. 7).

(2) Competitive ELISA

Competitive ELISA with use of the ASPD antibodies and 6E10 was performed using ELISA plates with solid-phase ASPD. Each antibody was caused to react with ASPD or sAPPα (Sigma) (room temperature, 1 hour) in a separate plate in advance, and was added to a ASPD solid-phase plate (already blocked with 1% BSA). Then, it was allowed to react at room temperature for 1 hour, and after it was subjected to washing, the detection was performed using a HRP-labeled secondary antibody.

As a result, as shown in Table 1, 6E10 and the mouse ASPD monoclonal antibodies disclosed in WO 2006/016644 exhibited reactivity with not only ASPD ($IC_{50}$=2.1 to 13 nM) but also sAPPα ($IC_{50}$=9.6 to 33.8 nM). On the other hand, the hamster antibodies exhibited reactivity with ASPD ($IC_{50}$=3.2 to 6.4 nM), but did not exhibit explicit reactivity with sAPPα ($IC_{50}$=>100 nM). These results show that the antibodies of the present invention react specifically with amylospheroids, and do not react with APP significantly. Thus, the antibodies of the present invention can be excellent, high-safety medicine with reduced side effects.

TABLE 2

| Antibody | Competitive ELISA/$IC_{50}$ (nM) | |
|---|---|---|
| | ASPD | sAPPα |
| mASD1 | 2.1 | 9.6 |
| mASD2 | 13.0 | 33.8 |
| mASD3 | 2.7 | 18.9 |
| haASD1 | 4.0 | >100 |
| haASD2 | 4.5 | >100 |
| haASD3 | 6.4 | >100 |
| haASD4 | 4.4 | >100 |
| haASD5 | 3.2 | >100 |
| 6E10 | 3.7 | 16.1 |

Example 7

Test Concerning Organ Specificity

Reactivities of antibodies with normal human tissues were evaluated.

In immunostaining with use of mouse antibodies, frozen human tissue sections were fixed in acetone, and were allowed to react with the peroxidase blocking solution in Envision Kit from DAKO for 5 minutes. They were allowed to react with a protein blocking solution containing 0.5% of casein, 1% of bovine serum albumin, 1.5% of normal goat serum, 2% of normal human immunoglobulin, and 1 mg/mL of thermally denatured human immunoglobulin for 20 minutes. Thereafter, antibodies diluted by PBS containing 1% of bovine serum albumin to a concentration of 2 or 10 mg/mL were added thereto, and were allowed to react at room temperature for 1 hour. After the peroxidase labeled polymer in Envision Kit from DAKO was allowed to react for 30 minutes, the DAB solution in Envision Kit from DAKO was added thereto and the reaction was allowed to proceed for 8 minutes. After the completion of each of the above-described steps, the samples were washed with PBS before being subjected to the next step. After the immunostaining was completed, the samples were washed with tap water, and were counterstained with hematoxylin.

In the immunostaining with use of hamster antibodies, glucose oxidase (2 U/mL)/glucose (10 mM) and sodium azide (1 mM) were added to acetone-fixed frozen sections at 35° for 1 hour, so that inherent peroxidase became inactive. After being blocked with avidin solution at room temperature for 15 minutes, and further, with biotin solution at room temperature for 15 minutes, the sections were allowed to react with a protein blocking solution containing 0.5% of casein, 1% of bovine serum albumin, 1.5% of normal goat serum, 5% of human immunoglobulin, and 1 mg/mL of thermally denatured human immunoglobulin at room temperature for 20 minutes. Thereafter, hamster antibodies diluted by PBS containing 1% of bovine serum albumin to a concentration of 2 or 10 mg/mL were added thereto, and were allowed to react at room temperature for 1 hour. Then, biotin-labeled goat anti-Armenian hamster IgG(H+L) antibodies were added thereto, and allowed to react at room temperature for 30 minutes. Further, ABC Elite reagent was allowed to react therewith for 30 minutes, and thereafter, DAB solution was allowed to react therewith at room temperature for 4 minutes.

All the mouse anti-ASPD antibodies and hamster anti-ASPD antibodies examined stained senile plaque-like structures in the frozen sections of Alzheimer's disease patients' cerebrums, which proved that substances recognized by these antibodies existed in Alzheimer's disease patients' cerebrums.

In experiments performed with respect to normal human cerebellum, spinal marrow, peripheral nerves, heart, liver, and kidney, many mouse anti-amylospheroid antibodies stained protein-like substances in blood vessels and therearound, nerve networks and neuronal cell nuclei in normal brain tissues, smooth muscles, muscle fiber blast cells, macrophages, Kupffer's cells, etc.

Some of the hamster anti-amylospheroid antibodies stained skeletal muscle cells and cardiac muscle cells, but their reactivity with normal human tissues were weaker as compared with those of the mouse antibodies. haASD1 and haASD2 hardly stained normal human tissues, and particularly regarding haASD2, no hot nodule was recognized at all for any normal tissues. The results are shown in FIG. 8 and Table 3.

TABLE 3

Comparison of positive immune-reactions detected in human tissue panels

| | mASD1 | mASD3 | haASD1 | haASD2 |
|---|---|---|---|---|
| Alzheimer's disease (senile plaque, neuronal basic fibril change) | +++ | +++ | +++ | +++ |
| Cerebellum (Purkinje, glia) | + | ± | ± | - |
| Heart | + | - | ± | - |
| Kidney | + | + | - | - |
| Liver | ++ | ± | - | - |
| Peripheral nerve | ++ (Schwann cell, as well) | ± | - | - |
| Spinal marrow | ++ | ++ | + | - |
| Blood vessel (endothelium, endovascular protein) | ++ | - | - | + (Vessel in chorioid plexus) |

The above-described results prove that the hamster monoclonal anti-amylospheroid antibodies of the present invention have low cross-reactivities with normal human tissues as compared with the conventionally known mouse monoclonal anti-amylospheroid antibodies, and are specific with Alzheimer's disease brains. Therapeutic antibodies based on this specificity of these hamster antibodies are expected to become therapeutic agents for Alzheimer's disease that do not affect tissues other than target organs thereby having low side effects.

Example 8

Verification of Antibody Specificity by Immunological Electron Microscope Observation

In physiological solvent environments, ASPD or fibrillar β-amyloid assembly was allowed to react with 10 μg/ml of the hamster antibody haASD1. The reaction was allowed to occur directly in a 1.5 ml tube or a carbon-deposited formvar grid. Thereafter, it was caused to further react with a 6 nm gold colloid-bound secondary antibody, negative-stained with uranium acetate, and subjected to electron microscope observation.

As shown in FIG. 9, the hamster antibody did not react with the fibrillar assembly, but was bound to amylospheroids.

Example 9

Immunohistochemical Analysis

Immunohistochemical analysis was performed by a commonly used method, using frozen sections of frozen brains, embedded in an optimum cutting temperature compound, and 10 μm thick sections of formalin-fixed brains, embedded in paraffin, obtained from 10 individuals suffering from Alzheimer's disease (age: 80.4±9.2 years, brain weight: 964±82 g, duration of disease: 10.1±5.5 years) and 7 control healthy individuals (age: 71.3±15.2 years, brain weight: 1226±96 g). Used as antibodies that recognize amylospheroids were the mouse monoclonal antibody mASD3, the hamster monoclonal antibody haASD1, and the rabbit polyclonal antibody rpASD2. Used as anti-amyloid β antibodies were a commercially-available anti-amyloid β antibody "IBL18582" (IBL), which recognizes a C-terminus of amyloid β-protein (Aβ1-42), and a commercially-available anti-amyloid β monoclonal antibody "6F/3D" (DAKO), which recognizes Aβ8-17.

As a result, all the antibodies that recognize amylospheroids (rpASD1, rpASD2, rpASD3, mASD3, haASD1) significantly stained plaques (senile plaque, diffuse senile plaque) present in basal forebrain, temporal cortex, and hippocampus of the frozen sections of Alzheimer's disease brains. This indicates in situ that amylospheroid-like structures were present in plaques. Besides, these antibodies except for haASD1 stained plaques in the formalin-fixed paraffin sections of brains as well, whether or not they had been subjected to microwave processing and formic acid processing. It should be noted that in normal control brains at the same age, structures other than microplaques were not stained. On the other hand, the commercially-available anti-amyloid β antibody "IBL18582", which recognizes a C-terminus of amyloid β-protein (Aβ1-42), and the commercially-available anti-amyloid β monoclonal antibody "6F/3D", which recognizes Aβ8-17, did not substantially stain plaques in frozen sections or paraffin sections of Alzheimer's disease brains that had not been subjected to microwave processing and formic acid processing. In view of these results, it was found that the antibodies that recognize amylospheroids specifically recognize the structure of amylospheroids, and among these antibodies, haASD1 in particular recognizes a tertiary structure more finely. This is consistent with the results of the antibody specificity verification by immunological electron microscope observation in Example 8, in which the amylospheroid antibody did not react with fibrillar assembly, but was bound to amylospheroids.

Example 10

Obtainment of Humanized Antibody and Analysis of the Same

(1) Obtainment of Humanized Antibody

RNA was obtained from the hybridoma haASD2 obtained in Example 2, which produces a hamster monoclonal antibody, using RNeasy Mini Kit (Cat. No. 74106) (QIAGEN). With use of this RNA as a genetic template, cDNA was synthesized, using $1^{st}$ Stand cDNA Synthesis Kit (Cat. No. 27-9261-01) (GE Life Sciences). As to the light chain variable domain, the cDNA was amplified with use of primers haVK1 and haCK, as well as Phusion High-Fidelity PCR Master Mix (Cat. No. F-531S) (Finnzymes), and it was joined with pCR-Blunt II-TOPO vector of Zero Blunt TOPO PCR Cloning Kit (Cat. No. 450245) (Invitrogen). As to the heavy chain variable domain, the cDNA was amplified with use of primers haVHf and MHCG3, as well as AdvantageR-HF 2 PCR Kit (Cat. No. 639123) (Clontech), and it was joint with pCR2.1-TOPO vector of TOPO-TA Cloning Kit (Cat. No. 450641) (Invitrogen). These were introduced to competent *Escherichia coli* cells TOP10 (Cat. No. 404003) (Invitrogen). Thereafter, as to clones having insertion DNA in intended sizes (VH: about 730 bp, VL: about 850 bp), base sequence thereof were analyzed and DNA sequences were determined, according to analysis entrusted to GATC Biotech.

TABLE 4

PCR primers for cloning hamster lambda VL

| Name | Sequence (5' → 3') |
|---|---|
| haVK1 | ATGGCTTGGACTCCTGGC (SEQ ID NO: 19) |
| haCK | GTCTTCACCCCATCATTGATAG (SEQ ID NO: 20) |

TABLE 5

PCR primers for cloning hamster VH

| Name | Sequence (5' → 3') |
|---|---|
| haVHf | ATGGGGTTGGGGCTGCACTGGG (SEQ ID NO: 21) |
| MHCG3 | CAAGGGATAGACAGATGGGGC (SEQ ID NO: 22) |

The complementarity-determining regions (CDRs) in the light chain and heavy chain variable domains in the hamster antibody were determined by the method of Kabat et al. ("Sequences of Proteins of Immunological Interest", Kabat, E., et al., US Department of Health and Human Services, (1983)), and the hamster antibody haASD2 was humanized by the method of Winter et al. disclosed in Japanese Patent No. 2912618. As a result, two types of humanized antibodies were obtained, which were named RHA/RLA (hereinafter referred to as huASD2 in some cases) and RHB/RLB, respectively.

An expression plasmid in which the heavy chain cDNA of the humanized antibody huASD2 was introduced was produced, which was named ASD2RHApG1D200. Further, an expression plasmid in which the light chain cDNA of the humanized antibody RHA/RLA was introduced was produced, which was named ASD2RLApLN100. ASD2RHApG1D200 and ASD2RLApLN100 were deposited at the International Patent Organism Depositary of the National Institute of Advanced Industrial Science and Technology (Tsukuba Central 6, 1-1-1 Higashi, Tsukuba, Ibaraki, Japan (Postal Code: 305-8566)) as of Oct. 17, 2008 under the receipt numbers of FERM ABP-11040 and FERM ABP-11041 (accession numbers FERM BP-11040 and FERM BP-11041), respectively.

The humanized antibody huASD2 can be obtained by cotransfecting ASD2RHApG1D200 and ASD2RLApLN100 into a known animal cell (e.g., CHO, NS0, HEK293, COS) and allowing the same to be expressed. One of the examples is transient expression in HEK293 with use of FREESTYLE MAX 293 EXP SYSTEM (Cat. No. K9000-10) (Invitrogen).

The DNA and amino acid sequences of the heavy chain variable domain of the humanized antibody huASD2 are shown in SEQ ID NOS: 4 and 5 in Sequence Listing and FIG. 10. In FIG. 10, the positions of CDRs 1, 2, and 3 are shown.

The DNA and amino acid sequences of the light chain variable domain of the humanized antibody huASD2 are shown in SEQ ID NOS: 6 and 7 in Sequence Listing and FIG. 11. In FIG. 11, the positions of CDRs 1, 2, and 3 are shown.

The humanized antibodies RHB/RLB can be obtained by producing plasmids that allow the heavy chain and the light chain to express, respectively, cotransfecting the same into an animal cell, and allowing the plasmids to express therein, like the humanized antibody huASD2.

The amino acid sequence of the heavy chain variable domain of the humanized antibody RHB/RLB is shown in SEQ ID NO: 8 in Sequence Listing and FIG. 12. The positions of CDRs 1, 2, and 3 are shown in FIG. 12.

The amino acid sequence of the light chain variable domain of the humanized antibody RHB/RLB is shown in SEQ ID NO: 9 in Sequence Listing and FIG. 13. The positions of CDRs 1, 2, and 3 are shown in FIG. 13.

Further, the humanized antibody RHC/RLC can be obtained by modifying the humanized antibody huASD2. The amino acid sequence of the heavy chain variable domain of the humanized antibody RHC/RLC was identical to the heavy chain variable domain of the humanized antibody huASD2. The amino acid sequence of the light chain variable domain of the humanized antibody RHC/RLC is as shown in SEQ ID NO: 10 in Sequence Listing and FIG. 14.

(2) Analysis of Humanized Antibody

Comparison between the amino acid sequences of the heavy chain and light chain variable domains of the humanized antibodies huASD2, RHB/RLB, and RHC/RLC is shown in FIG. 15. In the drawing, the heavy chain variable domain sequence of the humanized antibody huASD2 is indicated as "ASD2RHA"; the light chain variable domain sequence of the same is indicated as "ASD2RLA"; the heavy chain variable domain sequence of the humanized antibody RHB/RLB is indicated as "ASD2RHB"; the light chain variable domain sequence of the same is indicated as "ASD2RLB"; and the light chain variable domain sequence of the humanized antibody RHC/RLC is indicated as "ASD2RLC". The amino acid sequence of the heavy chain variable domain of the humanized antibody RHC/RLC is omitted in FIG. 15, since it is identical to the amino acid sequence of the heavy chain variable domain of the humanized antibody huASD2 (FIG. 15, ASD2RHA).

As seen in FIG. 15, the heavy chain variable domain of the humanized antibody RHB/RLB can be produced by replacing the amino acids at position 49 (G), position 81 (L), and position 100 (T) in the heavy chain variable domain of the humanized antibody huASD2, with A, V, and R, respectively. Further, the light chain variable domain of the humanized antibody RHB/RLB can be produced by replacing the amino acids at position 48 (Y), position 49 (L), position 51 (K), position 74 (A), and position 79 (G) in the light chain variable domain of the humanized antibody huASD2, with F, F, F, T, and A, respectively, In the amino acid residues shown in FIG. 15, the sequences other than the CDRs of the heavy chain variable domain (ASD2RHA) and the light chain variable domain (ASD2RLA) of the human antibody huASD2 were analyzed and were determined as being important in structural terms, by Medical Research Council (hereinafter abbreviated as MRCT) in accordance with the method of Winter et al. disclosed in Japanese Patent No. 2912618, and replacement of these will result in effective modification/alteration of huASD2 in its properties. More specifically, in the case where the humanized huASD2 and the hamster antibody haASD2 have functional differences, one or several portions, or all in the sequences may be reversed to the original sequences of the hamster antibody haASD2 (back mutation), whereby the reduction or elimination of such differences are expected. One example is the sequence RHB/RLB (SEQ ID NOS: 8 and 9, ASD2RHB and ASD2RLB in FIG. 15). However, from the viewpoint of decreasing the immunogenic properties of heterologous lead antibody with respect to humans, which is the purpose of the humanization, the amino acid replacement described herein is not a preferable operation, and is not needed to be carried out unless any effect that overwhelms the influences to the immunogenic properties is provided.

On the other hand, when the sequence of the human antibody AB021517 (GenBank No.) utilized in the design of the variable domain framework of huASD2 and the sequence of AJ241418 (the same) are compared with the genome sequences from which they are derived (V-segment and J-segment, respectively), hypermutation is perceived in the light chain (SEQ ID NOS: 6 and 7). The hypermutation is a mutation in the antigen-specific maturation process of the antibody, which occurs in the immunological environments reflecting individual genetic background. Therefore, without the genetic background, the hypermutation possibly indicates an immunogenic property, and this is considered to be one of the factors of unexpected immunogenic properties seen in the fully human antibody Humira.

As a means to avoid this, the following can be considered: reversing the hypermutated amino acid residues to the amino acid residues of the genome sequence common to humans. More specifically, one, two or all of the three hypermutated amino acid residues (the 2nd position (S), the 8th position (S), and the 51st position (K) in the amino acid sequence SEQ ID NO:7) in the light chain variable domain of huASD2 (FIG. 15, ASD2RLA) are replaced with A, A, and R, respectively, which are in accordance with the genome sequence (SEQ ID NO: 10, FIG. 15, ASD2RLC), within an extent that the influence to the properties of the antibody is acceptable.

Example 11

Analysis of Humanized Antibody Properties (1) Measurement of Dissociation Constant Through the same procedure as that in Example 3(3), 42ASPD, 40Aβ (Aβ monomer), and Aβ fibril (42 fibril) prepared from 42Aβ were coupled to CM5 sensor chips, and dissociation constants of the hamster antibody haASD2, the humanized antibody huASD2, and the anti-Aβ antibody 3D6 (US 20030165496 A1) with respect to the above-described proteins were determined. The anti-Aβ antibody 3D6 was produced as follows: synthesis genes corresponding to the mouse antibody light chain variable domain 3d6vl.aa and the synthesis gene corresponding to the heavy chain variable domain 3d6vh.aa of the same described in US 20030165496 A1 were produced by a conventional method, and were joined to the light chain constant domain and the heavy chain constant domain of a known mouse antibody, respectively, on the basis of the information of the aforementioned patent; by so doing, it was produced as a mouse IgG2b/κ molecule.

The results are shown in Table 6. The humanized antibody huASD2 exhibited a strong affinity (Kd $1.8\times10^{-10}$ M) with ASPD, which was about 580 times higher than with amyloid β-monomer, and about 6.4 times higher than with amyloid fibril. On the other hand, the affinity of the anti-Aβ antibody 3D6 with ASPD was about 34 times higher than with amyloid β-monomer, and about 2.0 times higher than with amyloid fibril. In other words, this shows that the humanized antibody huASD2 obtained herein had a higher selectivity with ASPD, as compared with the selectivity exhibited by the known Aβ antibody 3D6. Thus, the humanized antibody huASD2 of the present invention is expected to have a low side effect of cerebral microvascular hemorrhage, as it has a low affinity with Aβ40 deposited in cerebral blood vessels.

TABLE 6

Dissociation constants of antibodies

| Antibody | Affinity, Kd (nM) | | |
|---|---|---|---|
| | 42ASPD | 40Aβ | 42fibril |
| haASD2 | 0.0989 | 13.2 | 0.187 |
| huASD2 | 0.180 | 105 | 1.15 |
| 3D6 | 0.115 | 3.93 | 0.231 |

(2) Determination of Antigenic Determinant Region (Epitope) of Humanized Antibody huASD2

Which one of Aβ five residue peptides the humanized antibody huASD2 was joined to was examined using the same method as that in Example 4. As a result, it was clarified that the humanized antibody huASD2 was competitively inhibited, most potently by the N-terminus peptide (Aβ1-5) of the monomeric amyloid β-protein, as is the case with the hamster antibody haASD2.

Example 12

Evaluation of Cytotoxicity Neutralizing Activity by Humanized Antibody RHA/RLA

Embryos were taken out of 17 days pregnant rats (SD, Japan Charles River), and hippocampuses were dissected from their brains. Hippocampus primary culture neurons were prepared in the same manner as that in Example 5 of WO 2006/016644. More specifically, hippocampus neurons were cultured in a neuron culture medium (SUMMON) for 5 days (37° C., 5% $CO_2$). ASPD obtained by a known method (Proc. Natl. Acad. Sci. USA, 100, 6370-6375 (2003)) was used, which is called "DF-ASPD". DF-ASPD (0.35 μM), and haASD2 or huASD2 (7.5, 25 and 75 μg/ml) were incubated together at room temperature for 2 hours, and were directly added to the medium, to be cultured for 24 and 45 hours. As a control PBS(−) not containing any antibody was used. Thereafter, neuronal cell death was detected by cell death ELISA (Bosch) and propiodium iodide (PI) staining.

The neutralizing activities of haASD2 and huASD2 with respect to neuronal cell death by DF-ASPD were evaluated by cell death ELISA, as an apoptosis detection system, and the results are shown in FIG. 16. In FIG. 16, F12 represents a control not containing DF-ASPD. Addition of DF-ASPD (0.35 μM) caused the value of OD value (405-492 nm) to increase, with which cell death induction was confirmed (column of PBS(−) in DF-ASPD (0.35 μM). In contrast, in the cases of the addition of huASD2 as a humanized antibody of the hamster antibody haASD2, the OD values significantly decreased (columns of huASD2 (7.5, 25, and 75 in DF-ASPD (0.35 μM), which proves that huASD2 has a high effect of suppressing the neuronal cell death induced by DF-ASPD.

Next, the neutralizing activities of haASD2 and huASD2 antibodies (25 μg/ml) with respect to neuronal cell death by DF-ASPD were evaluated by detecting cell death using PI staining. The results are shown in FIG. 17. The detection of cell death was carried out by counting the number of PI positive cells per visual field. Like the case shown in FIG. 16, F12 represents the control not containing DF-ASPD, and PBS(−) represents a control not containing an antibody. Addition of DF-ASPD caused the number of PI-positive cells to significantly increase, with which apoptosis induction was confirmed (column of PBS(−) in DF-ASPD (0.35 μM)). In contrast, huASD2 and huASD2 exhibited a significant function of suppressing the number of PI-positive cells, which proves that they have a high effect of suppressing the neuronal cell death resulting from cell death induced by DF-ASPD.

Industrial Applicability

The antibody of the present invention has a low reactivity with amyloid precursor proteins, has a higher activity with amylospheroids than with amyloid β fibrils and with monomeric amyloid β-proteins, and further, has an activity of inhibiting the neuronal cell death induced by amylospheroids. Since amylospheroids induce neuronal cell death at a concentration equivalent to that of amyloid β-proteins that exist in the brains of patients with Alzheimer's disease, (1) an antibody having an activity of inhibiting the formation of amylospheroids, or (2) an antibody having an activity of inhibiting the neuronal cell death induced by amylospheroids, will be employed as a therapeutic or preventive agent for Alzheimer's disease. Further, (3) an antibody having a higher reactivity with amylospheroids than with monomeric amyloid β-proteins or with amyloid β fibrils will be possibly applied to the detection of individuals suffering from Alzheimer's disease. The antibody of the present invention has a low reactivity with amyloid precursor proteins, and has a high specificity with brains; thereby the antibody of the present invention will be a therapeutic agent for Alzheimer's disease having higher safety, as compared with the conventionally known anti-amylospheroid antibodies.

BRIEF DESCRIPTION OF DRAWINGS

FIG. 3 shows the results of analysis of epitopes of the monoclonal anti-amylospheroid specific antibodies of the present invention.

FIG. 10 shows a DNA sequence, an amino acid sequence, and positions of CDRs 1, 2, and 3 of the heavy chain variable domain of the humanized antibody RHA/RLA (huASD2).

FIG. 11 shows a DNA sequence, an amino acid sequence, and positions of CDRs 1, 2, and 3 of the light chain variable domain of the humanized antibody RHA/RLA (huASD2).

FIG. 12 shows an amino acid sequence and positions of CDRs 1, 2, and 3 of the heavy chain variable domain of the humanized antibody RHB/RLB.

FIG. 13 shows an amino acid sequence and positions of CDRs 1, 2, and 3 of the light chain variable domain of the humanized antibody RHB/RLB.

FIG. 14 shows an amino acid sequence and positions of CDRs 1, 2, and 3 of the light chain variable domain of the humanized antibody RHC/RLC.

SEQUENCE LISTING

Figure 1:
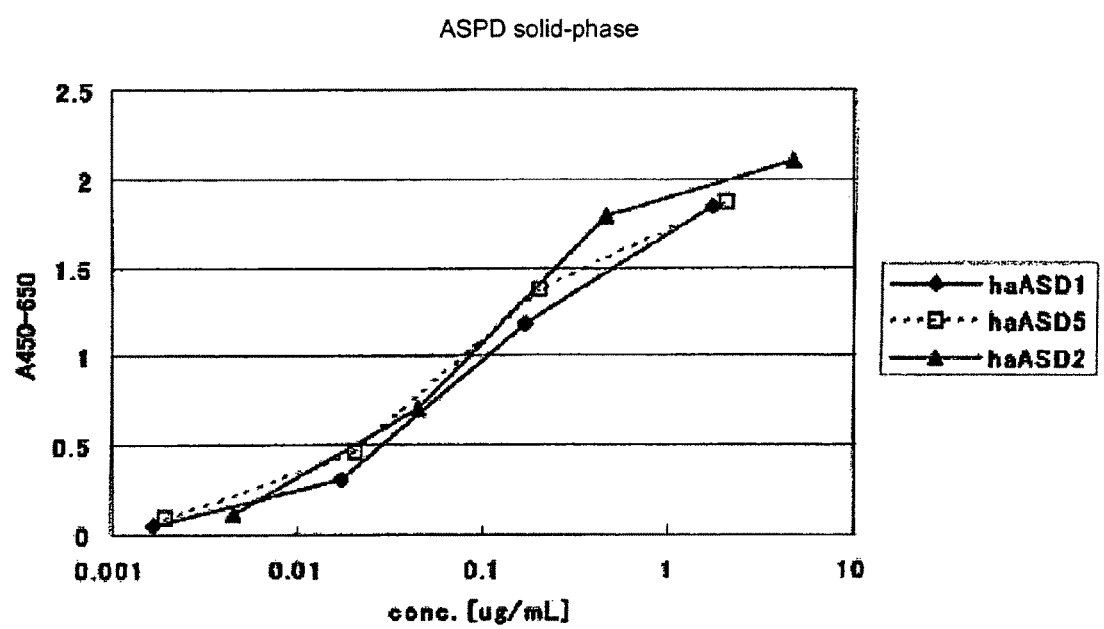
FIG. 1 is graph showing the results of solid-phase amylospheroid ELISA that analyzed creativities of the monoclonal anti-amylospheroid specific antibodies of the present invention
Figure 2:
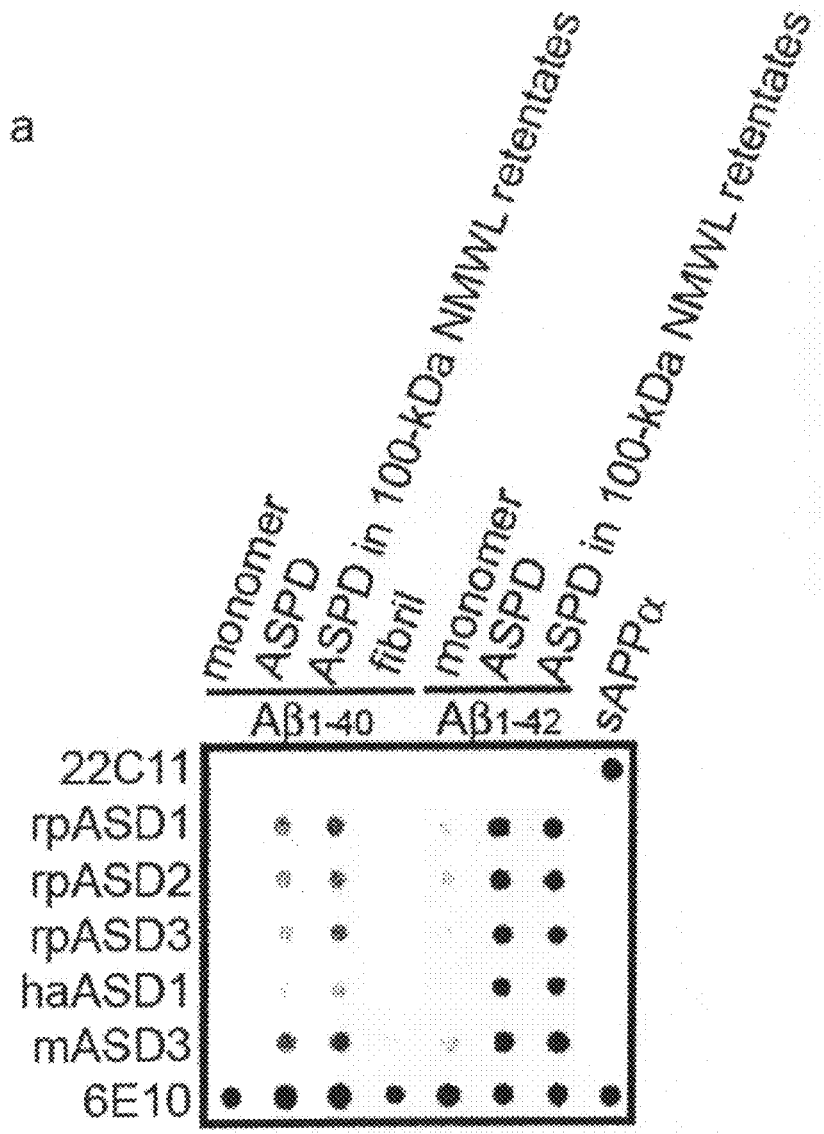
FIG. 2 is a graph showing the results of dot blotting that analyzed creativities of the monoclonal anti-amylospheroid specific antibodies of the present invention.
Figure 4:
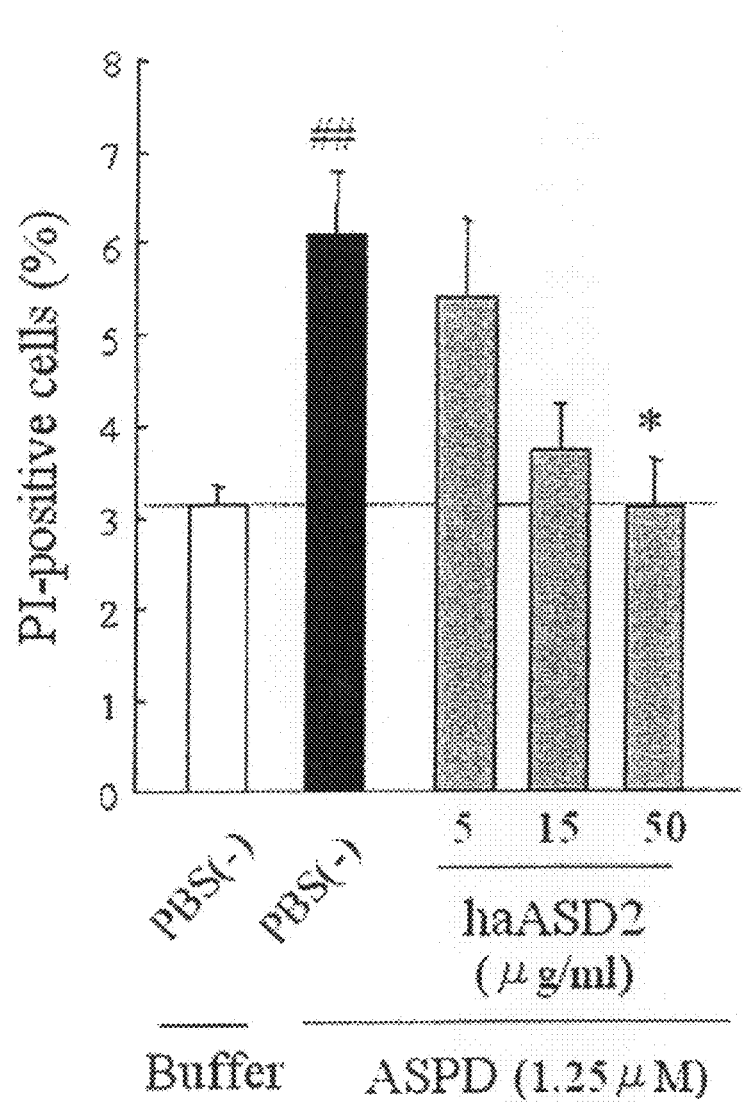
FIG. 4 is a graph showing the results of analysis of the activity of the monoclonal anti-amylospheroid specific antibodies of the present invention for inhibiting neuronal cell death induced by amylospheroids.
Figure 5:
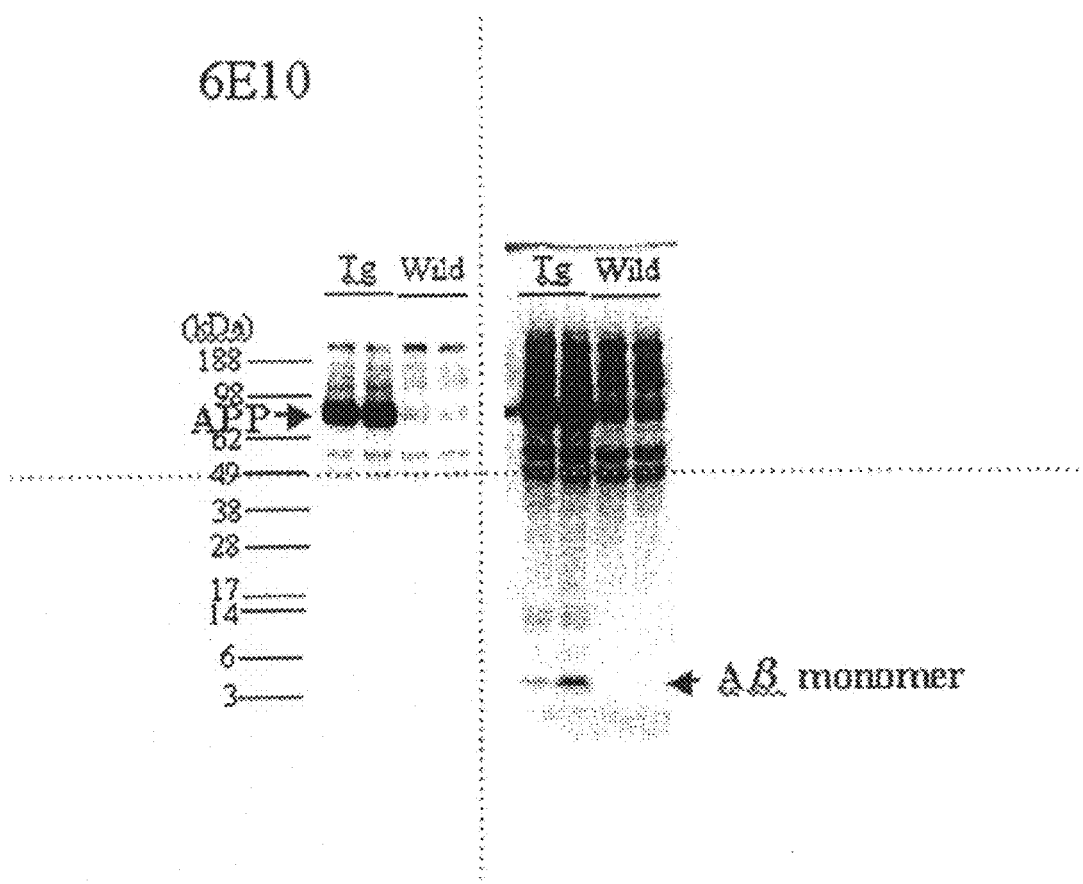
FIG. 5 is a graph showing the results of Western blotting that analyzed the reactivity of a commercially available antibody (6E 10).
Figure 6:
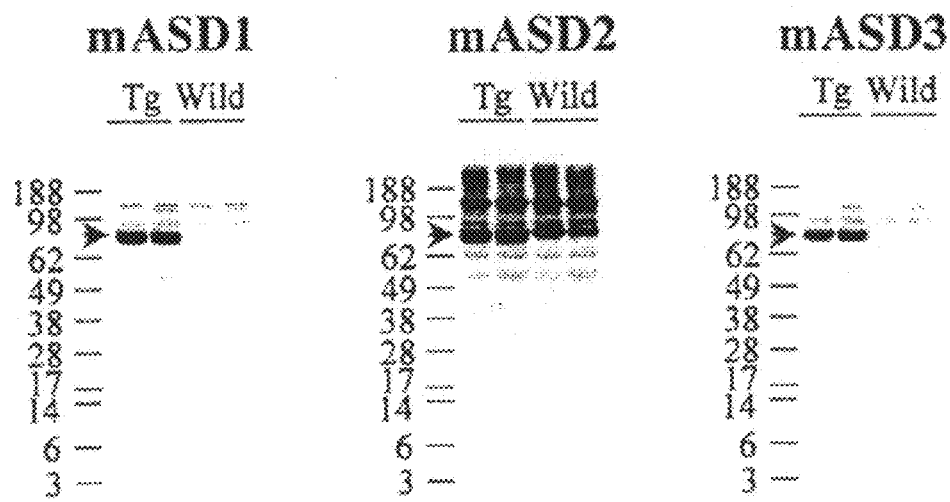
FIG. 6 is a graph showing the results of Western blotting that analyzed the reactivities of mouse monoclonal anti-amylospheroid antibodies (mASD1, mASD2, mASD3).
Figure 7:
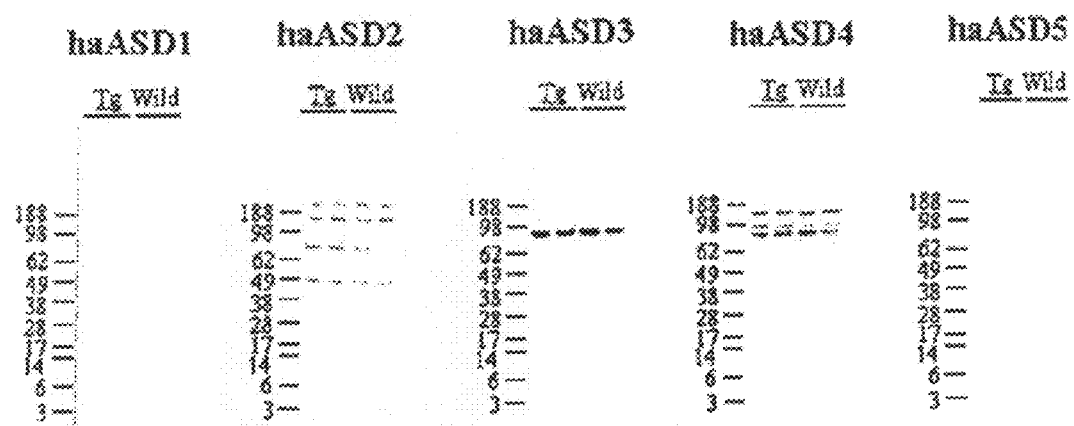
FIG. 7 is a graph showing the results of Western blotting that analyzed the reactivities of hamster monoclonal anti-amylospheroid antibodies of the present invention.
Figure 8:
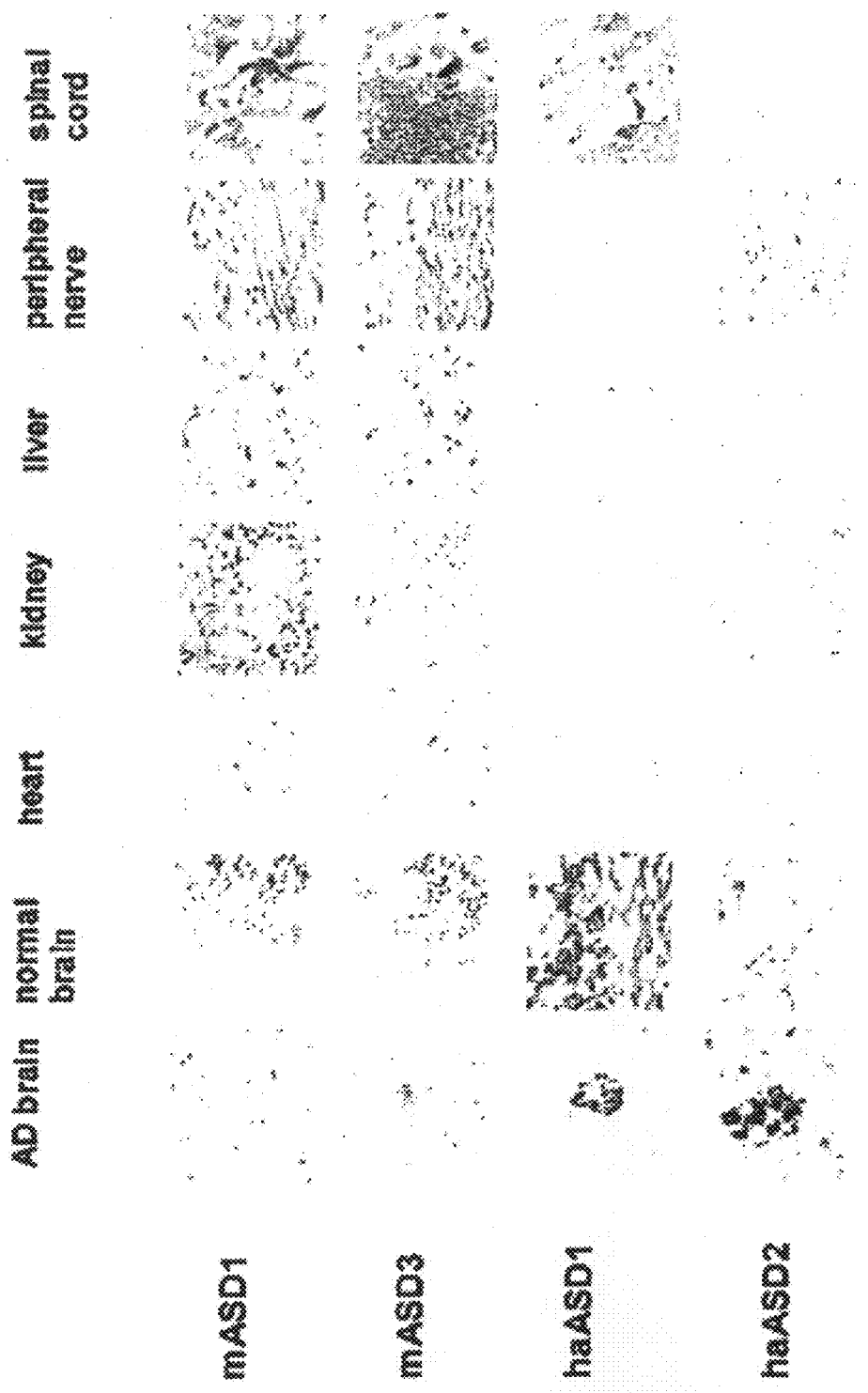
FIG. 8 shows reactivities of representative mouse monoclonal antibodies and hamster monoclonal antibodies with respect to normal human tissue panels.
Figure 9:
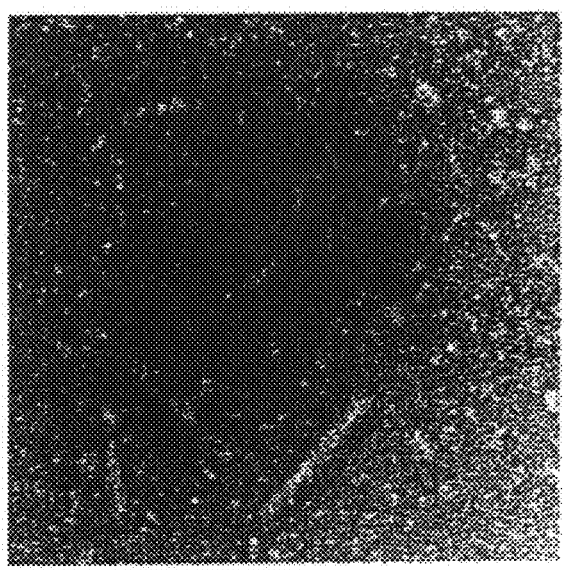
FIG. 9 shows electron microscope photographs showing antibody specificity with fibrillar β amyloid and ASPD.
Figure 15:
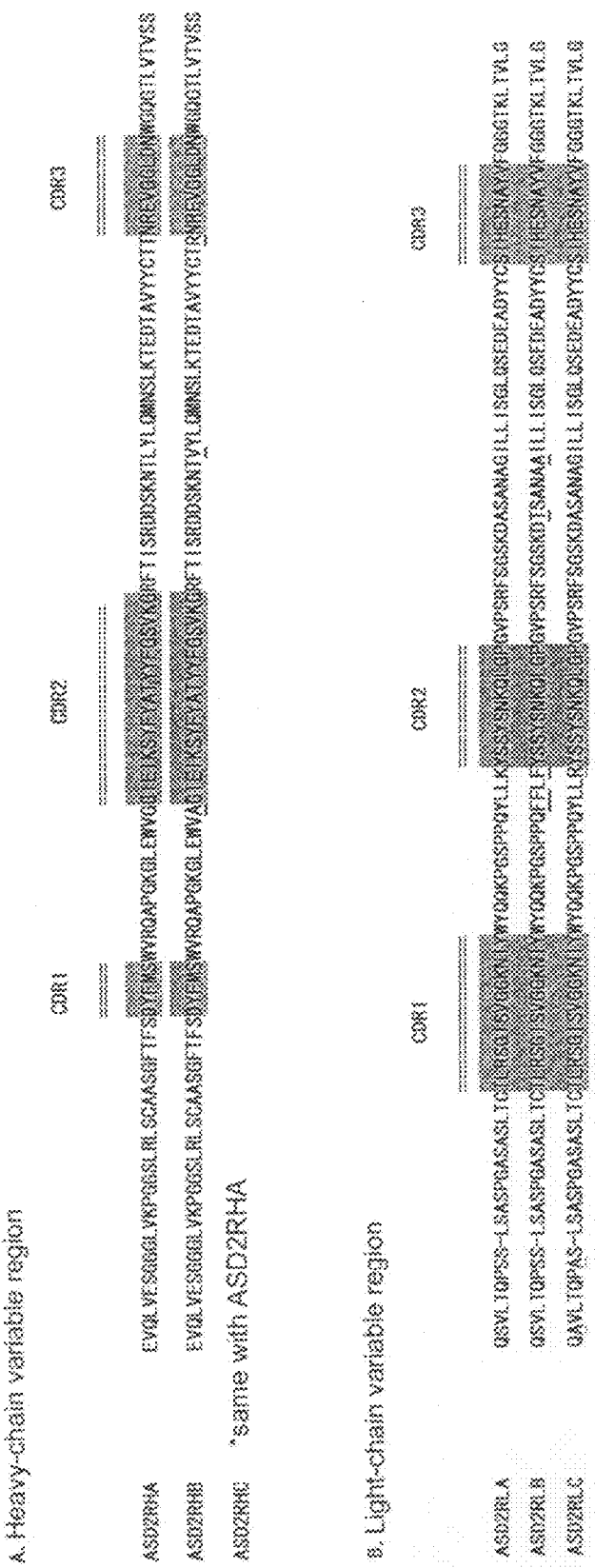
FIG. 15 compares amino acid sequences of the heavy and light chains of the three types of humanized antibodies obtained in the present invention, and indicates the positions of CDRs 1, 2, 3. The heavy chains of RHA/RLA (huASD2), RHB/RLB, and RHC/RLC are indicated as "ASD2RHA", "ASD2RHB", and "ASD2RHC", respectively. The illustration of sequence of ASD2RHC is omitted, since it is identical to the sequence of ASD2RHA. The light chains of RHA/RLA (huASD2), RHB/RLB, and RHC/RLC are indicated as "ASD2RLA", "ASD2RLB", and "ASD2RLC", respectively.
Figure 16:
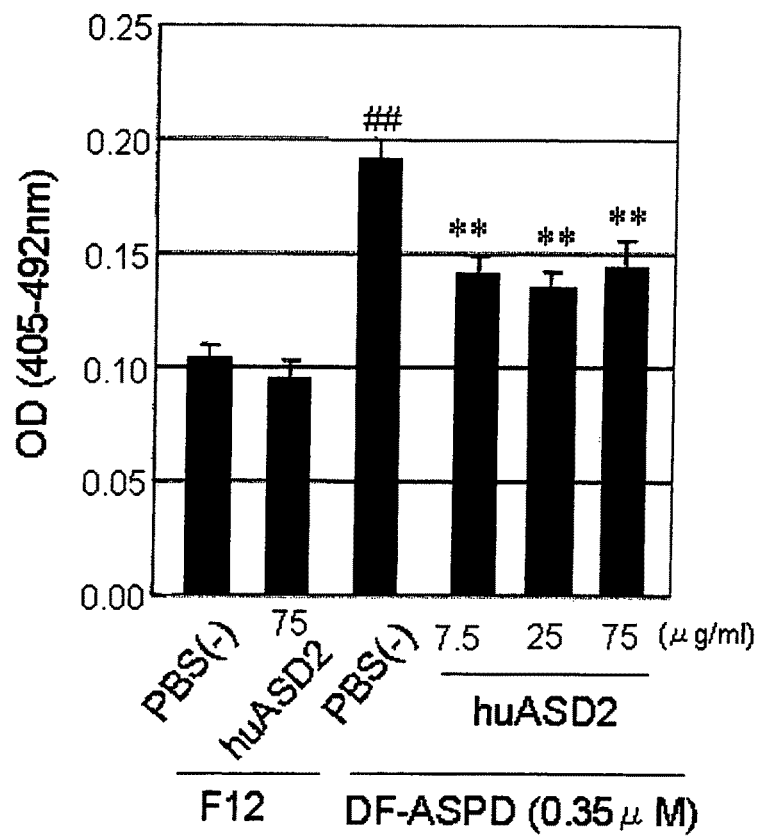
FIG. 16 shows an effect of huASD2 for inhibiting apoptosis induced by DF-ASPD.
Figure 17:
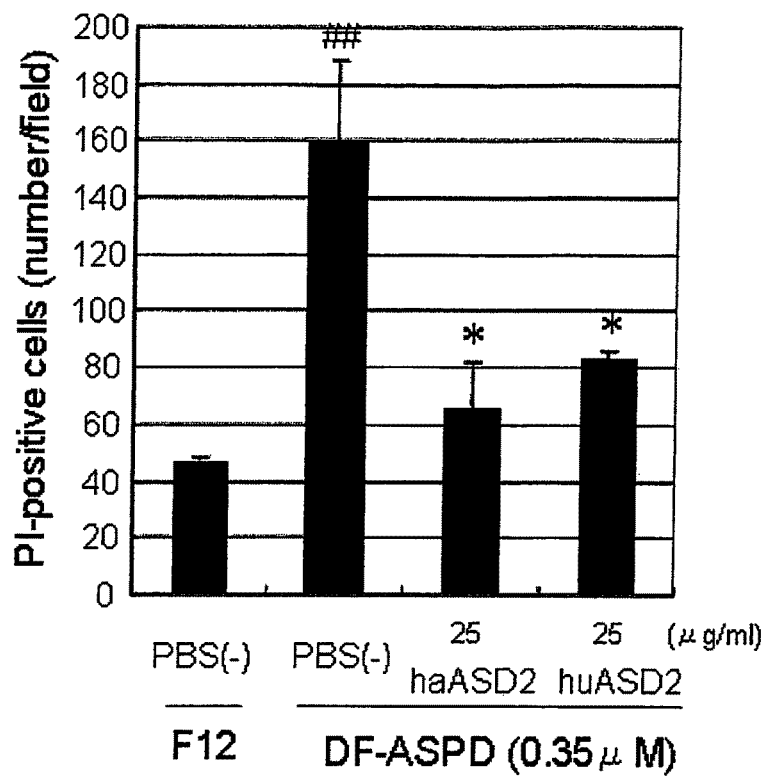
FIG. 17 shows an effect of haASD2 and huASD2 antibodies for inhibiting cell death induced by DF-ASPD.

```
<160> NUMBER OF SEQ ID NOS: 22

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30
```

```
Gly Leu Met Val Gly Gly Val Val Ile Ala
        35                  40

<210> SEQ ID NO 3
<211> LENGTH: 43
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 4
<211> LENGTH: 360
<212> TYPE: DNA
<213> ORGANISM: Artificial Sequence
<220> FEATURE:
<223> OTHER INFORMATION: Synthetic construct; humanized antibody
<220> FEATURE:
<221> NAME/KEY: CDS
<222> LOCATION: (1)..(360)

<400> SEQUENCE: 4 gaa gtg cag ctg gtc gag tct ggc ggc gga ctc gtg aag cct ggc ggc      48
Glu Val Gln Leu Val Glu Ser Gly Gly Gly Leu Val Lys Pro Gly Gly
1               5                   10                  15 tcc ctg cgg ctg tcc tgc gcc gcc tcc ggc ttt acc ttc tcc gac tac      96
Ser Leu Arg Leu Ser Cys Ala Ala Ser Gly Phe Thr Phe Ser Asp Tyr
            20                  25                  30 ttc atg tcc tgg gtg cgg cag gct cct ggc aag ggc ctg gaa tgg gtc     144
Phe Met Ser Trp Val Arg Gln Ala Pro Gly Lys Gly Leu Glu Trp Val
        35                  40                  45 ggg ggg atc gag atc aag tcc tac ttc tac gcc acc tac tac ttc ggc     192
Gly Gly Ile Glu Ile Lys Ser Tyr Phe Tyr Ala Thr Tyr Tyr Phe Gly
    50                  55                  60 tcc gtg aag ggc cgg ttc acc atc tcc cgg gac gac tcc aag aac acc     240
Ser Val Lys Gly Arg Phe Thr Ile Ser Arg Asp Asp Ser Lys Asn Thr
65                  70                  75                  80 ctg tac ctg cag atg aac tcc ctg aaa acc gag gac acc gcc gtg tac     288
Leu Tyr Leu Gln Met Asn Ser Leu Lys Thr Glu Asp Thr Ala Val Tyr
                85                  90                  95 tac tgc acc acc aac cgg gaa gtg ggg ggc ctg gac aac tgg ggc cag     336
Tyr Cys Thr Thr Asn Arg Glu Val Gly Gly Leu Asp Asn Trp Gly Gln
            100                 105                 110 ggc acc ctg gtg acc gtg tcc tcc                                     360
Gly Thr Leu Val Thr Val Ser Ser
        115                 120

<210> SEQ ID NO 5
<211> LENGTH: 120
<212> TYPE: PRT
<213> ORGANISM: Artificial Sequence
<220> FEATURE:
<223> OTHER INFORMATION: Synthetic construct; humanized antibody

<400> SEQUENCE: 5

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30
```

```
Phe Met Ser Trp Val Arg Gln Ala Pro Gly Lys Gly Leu Glu Trp Val
         35                  40                  45
Gly Gly Ile Glu Ile Lys Ser Tyr Phe Tyr Ala Thr Tyr Tyr Phe Gly
 50                  55                  60
Ser Val Lys Gly Arg Phe Thr Ile Ser Arg Asp Asp Ser Lys Asn Thr
 65                  70                  75                  80
Leu Tyr Leu Gln Met Asn Ser Leu Lys Thr Glu Asp Thr Ala Val Tyr
                 85                  90                  95
Tyr Cys Thr Thr Asn Arg Glu Val Gly Gly Leu Asp Asn Trp Gly Gln
                100                 105                 110
Gly Thr Leu Val Thr Val Ser Ser
            115                 120

<210> SEQ ID NO 6
<211> LENGTH: 351
<212> TYPE: DNA
<213> ORGANISM: Artificial Sequence
<220> FEATURE:
<223> OTHER INFORMATION: Synthetic construct; humanized antibody
<220> FEATURE:
<221> NAME/KEY: CDS
<222> LOCATION: (1)..(351)

<400> SEQUENCE: 6 cag tcc gtg ctg acc cag cct tcc tcc ctg tcc gcc tcc cct ggc gcc      48
Gln Ser Val Leu Thr Gln Pro Ser Ser Leu Ser Ala Ser Pro Gly Ala
 1               5                  10                  15 tcc gcc tcc ctg acc tgc acc ctg cgg tcc ggc atc tcc gtg ggc ggc      96
Ser Ala Ser Leu Thr Cys Thr Leu Arg Ser Gly Ile Ser Val Gly Gly
             20                  25                  30 aag aac atc tac tgg tat cag cag aag cct ggc tcc cct cct cag tac     144
Lys Asn Ile Tyr Trp Tyr Gln Gln Lys Pro Gly Ser Pro Pro Gln Tyr
         35                  40                  45 ctg ctg aag tac tcc tcc tac tcc aac aag cag ctg gga cct ggc gtg     192
Leu Leu Lys Tyr Ser Ser Tyr Ser Asn Lys Gln Leu Gly Pro Gly Val
 50                  55                  60 cct tcc cgg ttc tcc ggc tcc aag gac gcc agc gcc aac gcc ggc atc     240
Pro Ser Arg Phe Ser Gly Ser Lys Asp Ala Ser Ala Asn Ala Gly Ile
 65                  70                  75                  80 ctg ctg atc tct gga ctg cag agc gag gac gag gcc gac tac tac tgc     288
Leu Leu Ile Ser Gly Leu Gln Ser Glu Asp Glu Ala Asp Tyr Tyr Cys
                 85                  90                  95 tcc atc cac gag tcc aac gcc tac gtg ttt ggc ggc gga aca aag ctg     336
Ser Ile His Glu Ser Asn Ala Tyr Val Phe Gly Gly Gly Thr Lys Leu
                100                 105                 110 aca gtc ctg ggc cgg                                                  351
Thr Val Leu Gly Arg
        115

<210> SEQ ID NO 7
<211> LENGTH: 117
<212> TYPE: PRT
<213> ORGANISM: Artificial Sequence
<220> FEATURE:
<223> OTHER INFORMATION: Synthetic construct; humanized antibody

<400> SEQUENCE: 7

Gln Ser Val Leu Thr Gln Pro Ser Ser Leu Ser Ala Ser Pro Gly Ala
 1               5                  10                  15

Ser Ala Ser Leu Thr Cys Thr Leu Arg Ser Gly Ile Ser Val Gly Gly
             20                  25                  30
```

Lys Asn Ile Tyr Trp Tyr Gln Gln Lys Pro Gly Ser Pro Gln Tyr
        35                  40                  45

Leu Leu Lys Tyr Ser Ser Tyr Ser Asn Lys Gln Leu Gly Pro Gly Val
 50                  55                  60

Pro Ser Arg Phe Ser Gly Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                 85                  90                  95

Ser Ile His Glu Ser Asn Ala Tyr Val Phe Gly Gly Gly Thr Lys Leu
                100                 105                 110

Thr Val Leu Gly Arg
        115

<210> SEQ ID NO 8
<211> LENGTH: 120
<212> TYPE: PRT
<213> ORGANISM: Artificial Sequence
<220> FEATURE:
<223> OTHER INFORMATION: Synthetic construct; humanized antibody

<400> SEQUENCE: 8

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Phe Met Ser Trp Val Arg Gln Ala Pro Gly Lys Gly Leu Glu Trp Val
            35                  40                  45

Ala Gly Ile Glu Ile Lys Ser Tyr Phe Tyr Ala Thr Tyr Tyr Phe Gly
        50                  55                  60

Ser Val Lys Gly Arg Phe Thr Ile Ser Arg Asp Asp Ser Lys Asn Thr
 65                  70                  75                  80

Val Tyr Leu Gln Met Asn Ser Leu Lys Thr Glu Asp Thr Ala Val Tyr
                 85                  90                  95

Tyr Cys Thr Arg Asn Arg Glu Val Gly Gly Leu Asp Asn Trp Gly Gln
                100                 105                 110

Gly Thr Leu Val Thr Val Ser Ser
        115                 120

<210> SEQ ID NO 9
<211> LENGTH: 116
<212> TYPE: PRT
<213> ORGANISM: Artificial Sequence
<220> FEATURE:
<223> OTHER INFORMATION: Synthetic construct; humanized antibody

<400> SEQUENCE: 9

Gln Ser Val Leu Thr Gln Pro Ser Ser Leu Ser Ala Ser Pro Gly Ala
 1               5                  10                  15

Ser Ala Ser Leu Thr Cys Thr Leu Arg Ser Gly Ile Ser Val Gly Gly
                20                  25                  30

Lys Asn Ile Tyr Trp Tyr Gln Gln Lys Pro Gly Ser Pro Gln Phe
        35                  40                  45

Phe Leu Phe Tyr Ser Ser Tyr Ser Asn Lys Gln Leu Gly Pro Gly Val
 50                  55                  60

Pro Ser Arg Phe Ser Gly Ser Lys Asp Thr Ser Ala Asn Ala Ala Ile
 65                  70                  75                  80

Leu Leu Ile Ser Gly Leu Gln Ser Glu Asp Glu Ala Asp Tyr Tyr Cys
                 85                  90                  95

```
Ser Ile His Glu Ser Asn Ala Tyr Val Phe Gly Gly Gly Thr Lys Leu
            100                 105                 110

Thr Val Leu Gly
        115

<210> SEQ ID NO 10
<211> LENGTH: 116
<212> TYPE: PRT
<213> ORGANISM: Artificial Sequence
<220> FEATURE:
<223> OTHER INFORMATION: Synthetic construct; humanized antibody

<400> SEQUENCE: 10

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ile Ser Val Gly Gly
            20                  25                  30

Lys Asn Ile Tyr Trp Tyr Gln Gln Lys Pro Gly Ser Pro Pro Gln Tyr
        35                  40                  45

Leu Leu Arg Tyr Ser Ser Tyr Ser Asn Lys Gln Leu Gly Pro Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Ser Ile His Glu Ser Asn Ala Tyr Val Phe Gly Gly Gly Thr Lys Leu
            100                 105                 110

Thr Val Leu Gly
        115

<210> SEQ ID NO 11
<211> LENGTH: 5
<212> TYPE: PRT
<213> ORGANISM: Artificial Sequence
<220> FEATURE:
<223> OTHER INFORMATION: Synthetic construct; recombinant antibody

<400> SEQUENCE: 11

Asp Tyr Phe Met Ser
1               5

<210> SEQ ID NO 12
<211> LENGTH: 19
<212> TYPE: PRT
<213> ORGANISM: Artificial Sequence
<220> FEATURE:
<223> OTHER INFORMATION: Synthetic construct; recombinant antibody

<400> SEQUENCE: 12

Gly Ile Glu Ile Lys Ser Tyr Phe Tyr Ala Thr Tyr Tyr Phe Gly Ser
1               5                   10                  15

Val Lys Gly

<210> SEQ ID NO 13
<211> LENGTH: 9
<212> TYPE: PRT
<213> ORGANISM: Artificial Sequence
<220> FEATURE:
<223> OTHER INFORMATION: Synthetic construct; recombinant antibody

<400> SEQUENCE: 13

Asn Arg Glu Val Gly Gly Leu Asp Asn
1               5
```

<210> SEQ ID NO 14
<211> LENGTH: 14
<212> TYPE: PRT
<213> ORGANISM: Artificial Sequence
<220> FEATURE:
<223> OTHER INFORMATION: Synthetic construct; recombinant antibody

<400> SEQUENCE: 14

```
Thr Leu Arg Ser Gly Ile Ser Val Gly Gly Lys Asn Ile Tyr
1               5                   10
```

<210> SEQ ID NO 15
<211> LENGTH: 11
<212> TYPE: PRT
<213> ORGANISM: Artificial Sequence
<220> FEATURE:
<223> OTHER INFORMATION: Synthetic construct; recombinant antibody

<400> SEQUENCE: 15

```
Tyr Ser Ser Tyr Ser Asn Lys Gln Leu Gly Pro
1               5                   10
```

<210> SEQ ID NO 16
<211> LENGTH: 9
<212> TYPE: PRT
<213> ORGANISM: Artificial Sequence
<220> FEATURE:
<223> OTHER INFORMATION: Synthetic construct; recombinant antibody

<400> SEQUENCE: 16

```
Ser Ile His Glu Ser Asn Ala Tyr Val
1               5
```

<210> SEQ ID NO 17
<211> LENGTH: 120
<212> TYPE: PRT
<213> ORGANISM: Artificial Sequence
<220> FEATURE:
<223> OTHER INFORMATION: Synthetic construct; recombinant antibody
<220> FEATURE:
<221> NAME/KEY: MISC_FEATURE
<222> LOCATION: (49)..(49)
<223> OTHER INFORMATION: Xaa stands for Gly or Ala
<220> FEATURE:
<221> NAME/KEY: MISC_FEATURE
<222> LOCATION: (81)..(81)
<223> OTHER INFORMATION: Xaa stands for Leu or Val
<220> FEATURE:
<221> NAME/KEY: MISC_FEATURE
<222> LOCATION: (100)..(100)
<223> OTHER INFORMATION: Xaa stands for Thr or Arg

<400> SEQUENCE: 17

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Phe Met Ser Trp Val Arg Gln Ala Pro Gly Lys Gly Leu Glu Trp Val
        35                  40                  45

Xaa Gly Ile Glu Ile Lys Ser Tyr Phe Tyr Ala Thr Tyr Tyr Phe Gly
    50                  55                  60

Ser Val Lys Gly Arg Phe Thr Ile Ser Arg Asp Asp Ser Lys Asn Thr
65                  70                  75                  80

Xaa Tyr Leu Gln Met Asn Ser Leu Lys Thr Glu Asp Thr Ala Val Tyr
                85                  90                  95
```

```
Tyr Cys Thr Xaa Asn Arg Glu Val Gly Gly Leu Asp Asn Trp Gly Gln
            100                 105                 110

Gly Thr Leu Val Thr Val Ser Ser
        115                 120
```

<210> SEQ ID NO 18
<211> LENGTH: 116
<212> TYPE: PRT
<213> ORGANISM: Artificial Sequence
<220> FEATURE:
<223> OTHER INFORMATION: Synthetic construct; recombinant antibody
<220> FEATURE:
<221> NAME/KEY: MISC_FEATURE
<222> LOCATION: (2)..(2)
<223> OTHER INFORMATION: Xaa stands for Ser or Ala
<220> FEATURE:
<221> NAME/KEY: MISC_FEATURE
<222> LOCATION: (8)..(8)
<223> OTHER INFORMATION: Xaa stands for Ser or Ala
<220> FEATURE:
<221> NAME/KEY: MISC_FEATURE
<222> LOCATION: (48)..(48)
<223> OTHER INFORMATION: Xaa stands for Tyr or Phe
<220> FEATURE:
<221> NAME/KEY: MISC_FEATURE
<222> LOCATION: (49)..(49)
<223> OTHER INFORMATION: Xaa stands for Leu or Phe
<220> FEATURE:
<221> NAME/KEY: MISC_FEATURE
<222> LOCATION: (51)..(51)
<223> OTHER INFORMATION: Xaa stands for Lys, Phe or Arg
<220> FEATURE:
<221> NAME/KEY: MISC_FEATURE
<222> LOCATION: (74)..(74)
<223> OTHER INFORMATION: Xaa stands for Ala or Thr
<220> FEATURE:
<221> NAME/KEY: MISC_FEATURE
<222> LOCATION: (79)..(79)
<223> OTHER INFORMATION: Xaa stands for Gly or Ala

<400> SEQUENCE: 18

```
Gln Xaa Val Leu Thr Gln Pro Xaa Ser Leu Ser Ala Ser Pro Gly Ala
1               5                   10                  15

Ser Ala Ser Leu Thr Cys Thr Leu Arg Ser Gly Ile Ser Val Gly Gly
            20                  25                  30

Lys Asn Ile Tyr Trp Tyr Gln Gln Lys Pro Gly Ser Pro Pro Gln Xaa
        35                  40                  45

Xaa Leu Xaa Tyr Ser Ser Tyr Ser Asn Lys Gln Leu Gly Pro Gly Val
50                  55                  60

Pro Ser Arg Phe Ser Gly Ser Lys Asp Xaa Ser Ala Asn Ala Xaa Ile
65                  70                  75                  80

Leu Leu Ile Ser Gly Leu Gln Ser Glu Asp Glu Ala Asp Tyr Tyr Cys
                85                  90                  95

Ser Ile His Glu Ser Asn Ala Tyr Val Phe Gly Gly Gly Thr Lys Leu
            100                 105                 110

Thr Val Leu Gly
        115
```

<210> SEQ ID NO 19
<211> LENGTH: 18
<212> TYPE: DNA
<213> ORGANISM: Artificial Sequence
<220> FEATURE:
<223> OTHER INFORMATION: Synthetic construct

<400> SEQUENCE: 19
atggcttgga ctcctggc                                                 18

```
<210> SEQ ID NO 20
<211> LENGTH: 22
<212> TYPE: DNA
<213> ORGANISM: Artificial Sequence
<220> FEATURE:
<223> OTHER INFORMATION: Synthetic construct

<400> SEQUENCE: 20
gtcttcaccc catcattgat ag                                              22

<210> SEQ ID NO 21
<211> LENGTH: 22
<212> TYPE: DNA
<213> ORGANISM: Artificial Sequence
<220> FEATURE:
<223> OTHER INFORMATION: Synthetic construct

<400> SEQUENCE: 21
atggggttgg ggctgcactg gg                                              22

<210> SEQ ID NO 22
<211> LENGTH: 21
<212> TYPE: DNA
<213> ORGANISM: Artificial Sequence
<220> FEATURE:
<223> OTHER INFORMATION: Synthetic construct

<400> SEQUENCE: 22
caagggatag acagatgggg c                                               21
```

The invention claimed is:

1. An isolated monoclonal antibody obtained from a hamster or obtained by humanization of hamster monoclonal antibody having a higher reactivity with amylospheroid than with amyloid precursor proteins, and having any one or more of the following properties:
 (i) a higher activity with amylospheroid than with amyloid β fibrils;
 (ii) a higher reactivity with amylospheroid than with monomeric amyloid β-proteins; and
 (iii) an activity of inhibiting the neuronal cell death induced by amylospheroid.

2. The antibody according to claim 1, exhibiting a reactivity with amylospheroid at least 3 times higher than its reactivity with amyloid β fibrils, in a system wherein a reactivity of an antibody with amylospheroid is compared with a reactivity of the antibody with amyloid β fibrils at the same antibody concentration, antibody amount, antigen protein concentration, and antigen protein amount.

3. The antibody according to claim 1, exhibiting a reactivity with amylospheroid at least 5 times higher than its reactivity with amyloid β fibrils, in a system wherein a reactivity of an antibody with amylospheroid is compared with a reactivity of the antibody with amyloid β fibrils at the same antibody concentration, antibody amount, antigen protein concentration, and antigen protein amount.

4. The antibody according to claim 1, exhibiting a reactivity with amylospheroid at least 50 times higher than its reactivity with monomeric amyloid β-proteins, in a system wherein a reactivity of an antibody with amylospheroid is compared with a reactivity of the antibody with monomeric amyloid β-proteins at the same antibody concentration, antibody amount, antigen protein concentration, and antigen protein amount.

5. The antibody according to claim 1, exhibiting a reactivity with amylospheroid at least 500 times higher than its reactivity with monomeric amyloid β-proteins, in a system wherein a reactivity of an antibody with amylospheroid is compared with a reactivity of the antibody with monomeric amyloid β-proteins at the same antibody concentration, antibody amount, antigen protein concentration, and antigen protein amount.

6. The antibody according to claim 1, being obtained using amylospheroid as an antigen.

7. The antibody according to claim 1, having a dissociation constant with amylospheroid of not more than $10^{-9}$.

8. The antibody according to claim 1, reacting specifically with Alzheimer's disease brains while not exhibiting a significant cross-reactivity with human normal tissues.

9. The antibody according to claim 1, recognizing an epitope specific to a tertiary structure of amylospheroid.

10. The antibody according to claim 1, being a monoclonal antibody produced from a hybridoma having an accession number of either FERM BP-10871 or FERM BP-10872.

11. A neuron protector comprising the antibody according to claim 1.

12. A reagent for detecting Alzheimer's disease, comprising the antibody according to claim 1.

13. A medicine comprising the antibody according to claim 1.

14. A therapeutic agent for Alzheimer's disease, comprising the antibody according to claim 1.

15. A hybridoma for producing the antibody according to claim 1.

16. A humanized antibody obtained by humanization of a hamster monoclonal antibody produced from a hybridoma having an accession number of either FERM BP-10871 or FERM BP-10872.

17. The humanized antibody according to claim 16, or a fragment of the humanized antibody according to claim 16, comprising a humanized heavy chain and a humanized light chain, the humanized heavy chain including:
three heavy chain complementarity-determining regions (CDRs) obtained from a hamster monoclonal antibody produced from the hybridoma having the accession number of FERM BP-10872, the three heavy chain CDRs being heavy chain CDRs 1 to 3; and
a heavy chain variable domain framework sequence obtained from a human immunoglobulin heavy chain; and the humanized light chain including:
three light chain complementarity-determining regions (CDRs) obtained from a hamster monoclonal antibody produced from the hybridoma having the accession number of FERM BP-10872, the three light chain CDRs being light chain CDRs 1 to 3; and
a light chain variable domain framework sequence obtained from a human immunoglobulin light chain,
wherein the three heavy chain CDRs 1 to 3 have the following amino acid sequences, respectively:

```
                                          (SEQ ID NO: 11)
heavy chain CDR1: Asp Tyr Phe Met Ser;

(SEQ ID NO 12)
heavy chain CDR2: Gly Ile Glu Ile Lys Ser Tyr Phe
Tyr Ala Thr Tyr Tyr Phe Gly Ser Val Lys Gly;
``` and

```
                                          (SEQ ID NO: 13)
heavy chain CDR3: Asn Arg Glu Val Gly Gly Leu Asp
Asn,
``` and the three light chain CDRs 1 to 3 have the following amino acid sequences, respectively:

```
                                          (SEQ ID NO: 14)
light chain CDR1: Thr Leu Arg Ser Gly Ile Ser Val
Gly Gly Lys Asn Ile Tyr;

(SEQ ID NO: 15)
light chain CDR2: Tyr Ser Ser Tyr Ser Asn Lys Gln
Leu Gly Pro;
and (SEQ ID NO: 16)
light chain CDR3: Ser Ile His Glu Ser Asn Ala Tyr
Val.
```

18. The humanized antibody according to claim 16, or a fragment of the humanized antibody according to claim 16, comprising a humanized heavy chain variable domain having an amino acid sequence according to SEQ ID NO: 17; and a light chain variable domain having an amino acid sequence according to SEQ ID NO: 18, wherein the amino acid sequence according to SEQ ID NO: 17 is as follows:

```
[Chemical Formula 1]
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Phe Met Ser Trp Val Arg Gln Ala Pro Gly Lys Gly Leu Glu Trp Val
        35                  40                  45

Xaa Gly Ile Glu Ile Lys Ser Tyr Phe Tyr Ala Thr Tyr Tyr Phe Gly
    50                  55                  60

Ser Val Lys Gly Arg Phe Thr Ile Ser Arg Asp Asp Ser Lys Asn Thr
65                  70                  75                  80

Xaa Tyr Leu Gln Met Asn Ser Leu Lys Thr Glu Asp Thr Ala Val Tyr
            85                  90                  95

Tyr Cys Thr Xaa Asn Arg Glu Val Gly Gly Leu Asp Asn Trp Gly Gln
            100                 105                 110

Gly Thr Leu Val Thr Val Ser Ser
        115                 120
``` where "Xaa" at position 49 is Gly or Ala, "Xaa" at position 81 is Leu or Val, and "Xaa" at position 100 is Thr or Arg, and the amino acid sequence according to SEQ ID NO. 18 is as follows:

```
[Chemical Formula 2]
Gln Xaa Val Leu Thr Gln Pro Xaa Ser Leu Ser Ala Ser Pro Gly Ala
1               5                   10                  15

Ser Ala Ser Leu Thr Cys Thr Leu Arg Ser Gly Ile Ser Val Gly Gly
            20                  25                  30

Lys Asn Ile Tyr Trp Tyr Gln Gln Lys Pro Gly Ser Pro Pro Gln Xaa
```

```
                35                      40                      45
Xaa Leu Xaa Tyr Ser Ser Tyr Ser Asn Lys Gln Leu Gly Pro Gly Val
        50                      55                  60

Pro Ser Arg Phe Ser Gly Ser Lys Asp Xaa Ser Ala Asn Ala Xaa Ile
65                      70                  75                  80

Leu Leu Ile Ser Gly Leu Gln Ser Glu Asp Glu Ala Asp Tyr Tyr Cys
                85                      90                  95

Ser Ile His Glu Ser Asn Ala Tyr Val Phe Gly Gly Gly Thr Lys Leu
            100                     105                 110

Thr Val Leu Gly
            115
``` where "Xaa" at position 2 is Ser or Ala, "Xaa" at position 8 is Ser or Ala, "Xaa" at position 48 is Tyr or Phe, "Xaa" at position 49 is Leu or Phe, "Xaa" at position 51 is Lys, Phe, or Arg, "Xaa" at position 74 is Ala or Thr, and "Xaa" at position 79 is Gly or Ala.

19. The humanized antibody or the fragment thereof according to claim 18,
  wherein the humanized heavy chain variable domain has an amino acid sequence according to SEQ ID NO:5, and the light chain variable domain has an amino acid sequence according to SEQ ID NO. 7.

20. A method for detecting an individual with Alzheimer's disease, the method comprising:
  bringing a biological sample obtained from an individual suspected of Alzheimer's disease into contact with the antibody according to claim 1; and
  determining whether or not a substance that reacts with the antibody exists in the sample.

21. A hybridoma having an accession number of either FERM BP-10871 or FERM BP-10872.

\* \* \* \* \*

UNITED STATES PATENT AND TRADEMARK OFFICE
CERTIFICATE OF CORRECTION

PATENT NO. : 8,445,649 B2  Page 1 of 1
APPLICATION NO. : 12/734359
DATED : May 21, 2013
INVENTOR(S) : Hoshi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 271 days.

Signed and Sealed this
Eighth Day of September, 2015

Michelle K. Lee
*Director of the United States Patent and Trademark Office*